(12) United States Patent
Nielsen et al.

(10) Patent No.: US 11,786,112 B2
(45) Date of Patent: Oct. 17, 2023

(54) ENDOSCOPE CONTROL SYSTEM

(71) Applicant: AMBU A/S, Ballerup (DK)

(72) Inventors: Martin Refslund Nielsen, Birkerød (DK); Martin Johst Christensen, Copenhagen (DK); Günter Wilhelm Schütz, Augsburg (DE)

(73) Assignee: AMBU A/S, Ballerup (DK)

( * ) Notice: Subject to any disclaimer, the term of this patent is extended or adjusted under 35 U.S.C. 154(b) by 83 days.

(21) Appl. No.: 17/241,882

(22) Filed: Apr. 27, 2021

(65) Prior Publication Data

US 2021/0338051 A1    Nov. 4, 2021

Related U.S. Application Data

(63) Continuation of application No. 17/239,372, filed on Apr. 23, 2021, and a continuation of application No. 17/239,373, filed on Apr. 23, 2021.

(30) Foreign Application Priority Data

Apr. 30, 2020  (EP) .................................... 20172237
Apr. 30, 2020  (EP) .................................... 20172238
Apr. 30, 2020  (EP) .................................... 20172242

(51) Int. Cl.
    *A61B 1/005*    (2006.01)
    *A61B 1/00*    (2006.01)
    (Continued)

(52) U.S. Cl.
    CPC .......... *A61B 1/0052* (2013.01); *A61B 1/0011* (2013.01); *A61B 1/0057* (2013.01); *B29C 65/58* (2013.01); *B29L 2031/753* (2013.01)

(58) Field of Classification Search
    CPC ........................... A61B 1/0052; A61B 1/0057
    See application file for complete search history.

(56) References Cited

U.S. PATENT DOCUMENTS 3,610,231 A   10/1971   Takahashi et al.
4,207,873 A    6/1980   Kruy
(Continued)

FOREIGN PATENT DOCUMENTS

EP   0306723 B1   3/1993
EP   0754429 B1   9/2004
(Continued)

OTHER PUBLICATIONS

Extended search report in related European Application No. 20172242. 8, dated Oct. 12, 2020, 7 pgs.
(Continued)

*Primary Examiner* — Anh Tuan T Nguyen
*Assistant Examiner* — Rynae E Boler
(74) *Attorney, Agent, or Firm* — Faegre Drinker Biddle & Reath LLP

(57) ABSTRACT

An endoscope control system for performing a bending operation in a disposable insertion endoscope, the endoscope control system including a control wheel connected to a wire drum for connection to a steering wire of the endoscope, whereby rotation of the control wheel controls the bending operation, and a multi-disc brake including a stack of at least three brake discs, wherein activation of the multi-disc brake changes the multi-disc brake from a released state to a braking state, a brake torque generated by the multi-disc brake in the braking state braking rotation of the control wheel, the brake torque in the released state being at least partially released.

22 Claims, 11 Drawing Sheets

(51) Int. Cl.
  *B29C 65/58* (2006.01)
  *B29L 31/00* (2006.01)

(56) References Cited

U.S. PATENT DOCUMENTS

| | | | |
|---|---|---|---|
| 4,461,282 A | 7/1984 | Ouchi et al. | |
| 4,473,301 A | 9/1984 | Namyslo | |
| 4,617,914 A | 10/1986 | Ueda | |
| 4,825,850 A | 5/1989 | Opie et al. | |
| 4,924,852 A | 5/1990 | Suzuki et al. | |
| 4,942,866 A | 7/1990 | Usami | |
| 5,014,685 A | 5/1991 | Takahashi | |
| 5,086,200 A | 2/1992 | Kline et al. | |
| 5,174,276 A | 12/1992 | Crockard | |
| 5,269,202 A | 12/1993 | Kiyosawa et al. | |
| 5,329,887 A | 7/1994 | Ailinger et al. | |
| 5,426,992 A | 6/1995 | Morii et al. | |
| 5,464,007 A | 11/1995 | Krauter et al. | |
| 5,507,717 A | 4/1996 | Kura et al. | |
| 5,512,035 A | 4/1996 | Konstorum et al. | |
| 5,575,755 A | 11/1996 | Krauter et al. | |
| 5,871,441 A | 2/1999 | Ishiguro et al. | |
| 5,888,192 A | 3/1999 | Heimberger | |
| 6,599,265 B2 | 7/2003 | Bon | |
| 6,656,111 B2 | 12/2003 | Fujii et al. | |
| 6,673,012 B2 | 1/2004 | Fujii et al. | |
| 6,821,282 B2 | 11/2004 | Perry et al. | |
| 7,510,107 B2 | 3/2009 | Timm et al. | |
| 7,588,176 B2 | 9/2009 | Timm et al. | |
| 7,633,837 B2 | 12/2009 | Daout | |
| 7,731,072 B2 | 6/2010 | Timm et al. | |
| 7,735,396 B2 | 6/2010 | Ishikawa et al. | |
| 7,926,379 B2 | 4/2011 | Gutmann et al. | |
| 8,042,423 B2 | 10/2011 | Bannier et al. | |
| 8,048,025 B2 | 11/2011 | Barenboym et al. | |
| 8,052,636 B2 | 11/2011 | Moll et al. | |
| 8,257,303 B2 | 9/2012 | Moll et al. | |
| 8,286,845 B2 | 10/2012 | Perry et al. | |
| 8,302,507 B2 | 11/2012 | Kanai | |
| 8,578,808 B2 | 11/2013 | Koitabashi | |
| 8,808,168 B2 | 8/2014 | Ettwein et al. | |
| 8,845,521 B2 | 9/2014 | Maruyama | |
| 8,904,894 B2 | 12/2014 | Geiser | |
| 8,911,362 B2 | 12/2014 | Kaneko | |
| 9,044,135 B2 | 6/2015 | Ishii et al. | |
| 9,044,138 B2 | 6/2015 | Sjostrom et al. | |
| 9,057,421 B2 | 6/2015 | Ishikawa et al. | |
| 9,155,865 B2 | 10/2015 | Golden et al. | |
| 9,237,837 B2 | 1/2016 | Omoto et al. | |
| 9,360,098 B2 | 6/2016 | Roopnarine | |
| 9,394,985 B2 | 7/2016 | Kobayashi et al. | |
| 9,457,168 B2 | 10/2016 | Moll et al. | |
| 9,534,681 B2 | 1/2017 | Ishikawa | |
| 9,545,253 B2 | 1/2017 | Worrell et al. | |
| 9,833,131 B2 | 12/2017 | Golden et al. | |
| 9,949,623 B2 | 4/2018 | Lang | |
| 10,085,623 B2 | 10/2018 | Osaki | |
| 10,197,153 B2 | 2/2019 | Dumanski et al. | |
| 10,203,022 B2 | 2/2019 | Atmur et al. | |
| 10,238,271 B2 | 3/2019 | Haraguchi | |
| 2001/0037051 A1* | 11/2001 | Fujii | A61B 1/0052 |
| | | | 600/146 |
| 2002/0019591 A1 | 2/2002 | Bon | |
| 2002/0099266 A1 | 7/2002 | Ogura et al. | |
| 2004/0010245 A1 | 1/2004 | Cerier et al. | |
| 2004/0015054 A1 | 1/2004 | Kazuhiko | |
| 2009/0149709 A1 | 6/2009 | Koitabashi | |
| 2009/0247828 A1 | 10/2009 | Watanabe et al. | |
| 2011/0118550 A1 | 5/2011 | Tulley | |
| 2011/0144440 A1 | 6/2011 | Cropper et al. | |
| 2011/0208001 A1 | 8/2011 | Haeckl et al. | |
| 2012/0277535 A1* | 11/2012 | Hoshino | A61B 1/00066 |
| | | | 600/146 |
| 2013/0204096 A1 | 8/2013 | Ku et al. | |
| 2013/0296848 A1* | 11/2013 | Allen, IV | A61B 18/1445 |
| | | | 606/41 |
| 2014/0058323 A1* | 2/2014 | Hoshino | G02B 23/2476 |
| | | | 604/95.04 |
| 2014/0142389 A1 | 5/2014 | Lim et al. | |
| 2014/0296640 A1* | 10/2014 | Hoshino | A61B 1/0052 |
| | | | 600/146 |
| 2014/0343489 A1* | 11/2014 | Lang | A61B 1/0052 |
| | | | 604/95.04 |
| 2015/0057537 A1 | 2/2015 | Dillon et al. | |
| 2015/0359415 A1 | 12/2015 | Ang et al. | |
| 2016/0067457 A1 | 3/2016 | Selkee | |
| 2018/0132899 A1 | 5/2018 | SooHoo | |
| 2019/0029498 A1 | 1/2019 | Mankowski et al. | |
| 2019/0035440 A1 | 1/2019 | Yuan et al. | |
| 2019/0209205 A1 | 7/2019 | Nishio | |
| 2019/0313884 A1 | 10/2019 | Isobe | |
| 2019/0350440 A1 | 11/2019 | Leong et al. | |
| 2021/0338049 A1 | 11/2021 | Christensen | |
| 2021/0338050 A1 | 11/2021 | Christensen et al. | |

FOREIGN PATENT DOCUMENTS

| | | |
|---|---|---|
| EP | 2594307 A1 | 5/2013 |
| EP | 2594307 A1 | 5/2013 |
| EP | 2692227 A1 | 2/2014 |
| EP | 2692277 A1 | 5/2014 |
| EP | 2594307 B1 | 9/2016 |
| EP | 2692227 B1 | 8/2018 |
| JP | H09-38028 | 2/1997 |
| JP | H0938028 A | 2/1997 |
| JP | 2005-160790 | 6/2017 |
| WO | 2008023965 A1 | 2/2008 |
| WO | WO2008023965 A1 | 2/2008 |
| WO | 2014/186519 A2 | 11/2014 |
| WO | 2018022402 A1 | 2/2018 |
| WO | 2018022418 A2 | 2/2018 |
| WO | WO2018022402 A1 | 2/2018 |
| WO | WO2018022418 A2 | 2/2018 |
| WO | 2018131305 A1 | 7/2018 |
| WO | 2021/213600 A1 | 10/2021 |

OTHER PUBLICATIONS

Extended search report in related European Application No. 20172237.8, dated Oct. 19, 2020, 8 pgs.

Extended search report in related European Application No. 20172238.6, dated Oct. 26, 2020, 10 pgs.

Jarrahy, "A new powered endoscope holding arm for endoscopic surgery of the cranial base," Min-Minimally Invasive Neurosurgery 45.03 (2002): 189-192.

Lerner, "A passive seven degree of freedom postitioning device for surgical robots and devices," MS thesis. Johns Hopkins University, 1998.

Jain, "Micromanipulator: effectiveness in minimally invasive neurosurgery", min-Minimally Invasive Neurosurgery 46.04 (2003): 235-239.

Poels, "Design of the frame and arms of a master for robotic surgery," DCT rapporten 2007 (2007).

Fedotov, "Industrial conical gear, cogwheel," dreamstime.com, ID 133121587, accessed: Apr. 2019.

Steine Lager, Wheel 32×64 Conical with Spikes and Inner 48 Tooth Gear 64712—Black, steinelager.de, accessed: Apr. 2019.

Extended European Search Report issued in EP20172238.6, dated Oct. 26, 2020, 9 pages.

Extended European Search Report issued in EP20172237.8, dated Oct. 19, 2020, 9 pages.

Extended European Search Report issued in EP20172242.8, dated Oct. 12, 2020, 8 pages.

Jarrahy et al., "A new powered endoscope holding arm for endoscopic surgery of the cranial base," Minim Invasive Neurosurg 2002; 45(3): 189-192.

Lerner, "A Passive Seven Degree of Freedom Postitioning Device for Surgical Robots and Devices," dissertation submitted to the Johns Hopkins University, Baltimore, Maryland, 1998.

Jain et al., "Micromanipulator: Effectiveness in Minimally Invasive Neurosurgery," Minim Invasive Neurosurg 2003; 46(4): 235-239.

(56) References Cited

OTHER PUBLICATIONS

Poels, Design of the Frame and Arms of a Master for Robotic Surgery, Traineeship report, Technische Universiteit Eindhoven, Department of Mechanical Engineer, Control Systems Technology Group, Jul. 2007.

Industrial conical gear, cogwheel, available at Dreamstime.com, website copyright 2000-2019.

eBay listing, steinelager.de, Wheel 32×64 Conical with Spikes and Inner 48 Tooth Gear 64712—Black, available at https://stenelager.de/en/categroy/7/wheel and https://www.steinelager.de/en/color/26/black, website copyright 2016-1029.

* cited by examiner

ENDOSCOPE CONTROL SYSTEM

CROSS-REFERENCE TO RELATED APPLICATIONS

The present application is a continuation of U.S. patent application Nos. 17/239,372 and 17/239,373, filed Apr. 23, 2021, and claims priority to and the benefit of European Patent Application Nos. 20172237.8, 20172238.6 and 20172242.8, filed Apr. 30, 2020; all said applications are incorporated by reference herein in their entirety.

TECHNICAL FIELD

The present disclosure relates to insertable medical vision devices, such as, but not limited to, endoscopes, in particular disposable insertion endoscopes, such as duodenoscopes, gastroscopes, and colonoscopes. More specifically, the present disclosure relates to endoscope control systems comprising control wheels connected to associated wire drums for connection to steering wires, whereby rotation of the control wheels controls a bending operation of a tip of the endoscope, and wherein activation of one or more brakes brake rotation of one or more control wheels.

BACKGROUND

Endoscopes are typically equipped with a light source and a vision receptor including a vision or image sensor. Provided that enough light is present, it is possible for the operator to see where the endoscope is steered and to set the target of interest once the tip has been advanced thereto.

Endoscopes typically comprise an elongated insertion tube with a handle at the proximal end, as seen from the operator, and visual inspection means, such as a built-in camera including a vision sensor, at a distal end of the elongated insertion tube. This definition of the terms distal and proximal, i.e. "proximal" being the end closest to the operator and "distal" being the end remote from the operator, as used herein for endoscopes in general, is adhered to in the present specification. Electrical wiring for the camera and other electronics, such as one or more LEDs accommodated in the tip part at the distal end, runs along the inside of the elongated insertion tube from the handle to the tip part. A working or suction channel may run along the inside of the insertion tube from the handle to the tip part, e.g. allowing liquid to be removed from the body cavity or allowing for insertion of surgical instruments or the like into the body cavity. The suction channel may be connected to a suction connector, typically positioned at a handle at the proximal end of the insertion tube.

To be able to maneuver the endoscope inside the body cavity, the distal end of some endoscopes comprises a bendable distal tip, which may be bendable in one, e.g. an up/down dimension, or two dimensions, e.g. an up/down dimension and a left/right dimension. The bendable tip often comprises a bending section with increased flexibility, e.g. achieved by articulated segments of the bending section. The maneuvering of the endoscope inside the body is typically done by tensioning or slacking steering wires also running along the inside of the elongated insertion tube from the tip part through the remainder of articulated segments to a control system or control mechanism positioned in or forming part of the handle.

An endoscope control system for performing a bending operation in two dimensions is known from WO2018022418A2. This control system includes two control wheels connected two associated wire drums for connection to associated steering wires of the endoscope, whereby rotation of the control wheels controls the bending operation in two dimensions. The control system includes a brake activated by a brake handle.

U.S. Pat. No. 9,949,623B discloses another endoscope control system including a control wheel and a brake.

U.S. Pat. No. 5,329,887 discloses another endoscope control system including two control wheels and in which a separately provided snap ring or snap clip attaches a control shaft.

In the prior art, other separate attachment means, such as locking rings or spring clips, have also been applied to attach parts to each other.

Furthermore, the control systems of the prior art are often assembled in a manner which requires flipping the parts around the already assembled parts during the method of assembly.

Multi-disc brakes, also known as multiple disc brakes, multi-plate brakes, or multiple plate brakes, are well-known in technical fields far removed from that of endoscopes, e.g. in heavy machinery in the pressing industry and winching machinery. Technically, these types of brakes are closely related to multi-disc clutches, also known as multiple disc clutches, multi-plate clutches, or multiple-plate clutches. Other well-known applications of multi-disc brakes include in machinery for agriculture, motorcycles, and race cars.

SUMMARY

A first aspect of this disclosure relates to an endoscope control system for performing a bending operation in a disposable insertion endoscope, the endoscope control system comprising: a control wheel connected to a wire drum for connection to a steering wire of the endoscope, whereby rotation of the control wheel controls the bending operation; and a multi-disc brake comprising a stack of at least three brake discs, wherein activation of the multi-disc brake changes the multi-disc brake from a released state to a braking state, a brake torque generated by the multi-disc brake in the braking state braking rotation of the control wheel, the brake torque in the released state being at least partially released.

With such a multi-disc brake, a relatively high braking torque may be achievable with relatively small dimensions, such as a diameter, of the brake. Load and friction may be shared between several and potentially larger friction interfaces, and a more consistent and predictable brake torque may be achievable.

Furthermore, such a multi-disc brake may make it possible to better control the braking torque (in the braking state), which should be high enough to leave a tip of the endoscope in a desired bent or unbent position, but not so high as to risk injury to or damaged tissue of a patient, e.g. if the physician by mistake should attempt to retract the tip from the patient without releasing the brake. In this case the tip must be allowed to move before any injuries to the tissue can take place. If the control system includes a spring as described further below, a smaller spring and/or a spring of lower spring constant may potentially be suitable, and tolerances of the spring force may be improved. A longer pre-loaded spring with a low spring constant may achieve a robust design and a lower long-term mechanical stress on surrounding elements, which may make it possible to manufacture such elements from materials of lower strength and/or rigidity, such as plastic polymers. See also further below.

Furthermore, such a multi-disc brake may be made compact and/or easy to engage and/or disengage and/or may be manufacturable with low cost while being able to withstand forces as required by the intended use and/or may be provided so that it achieves a consistent brake torque when engaged.

Furthermore, such a multi-disc brake may achieve a predictable and consistent brake torque. This may be advantageous in some applications where the brake torque should be within a specific range.

The multi-disc brake may be a friction brake which may work by friction members sliding on each other at a certain diameter across a rotation axis. One friction member may be attached to a frame and one friction member may be attached to a body of which movement is to be braked. A normal force may act on pairs of friction members, potentially resulting in a friction force working against movement at a contact diameter. This may result in a brake torque proportional with the normal force, contact diameter and a coefficient of friction.

In order to achieve a consistent brake torque within a specific range, pairs of friction members with consistent coefficient of friction can be applied. Friction members with a relatively consistent coefficient of friction (low variance of the coefficient of friction) typically have a relatively low coefficient of friction. Consistent and low coefficients of friction can be achieved with plastics materials, which may provide the possibility of using low cost injection molded components.

The pairs of friction members may slide at a limited diameter; hence, the brake may be compact in order to fit into a handle assembly of the endoscope. In a conventional friction brake, a combination of a low coefficient of friction and a limited working diameter may result in a need for a high normal force. A high normal force may not be desirable; hence, the brake may be dimensioned to be stronger and more rigid, which may compromise a desire to make a cheaper brake and a desire to make it easy to engage and disengage the brake. Multiple friction surfaces working in parallel may eliminate a need of a high normal force even though the coefficient of friction and the diameter are limited. Hence, the brake torque is proportional with the number of friction interfaces working in parallel. Multiple friction interfaces can be made in a simple way by stacking friction discs on top of each other. Every other disc may be rotationally attached to the frame, and the remaining discs in between may be attached to the body which is intended to be braked. A compression force on the disc stack may result in a similar normal force between each pair friction of friction members. Hence, a limited compression force on the stack may provide a sufficient brake torque (even though the coefficient of friction and the diameter are limited). This may limit the structural requirements of the brake components. A further advantage of having multiple sliding surfaces may be that heat generation and wear may be distributed between multiple interfaces. Reduced component requirements for structure, wear, heat resistance, and heat transfer may make it possible to use low cost, injection molded plastic parts.

It may be desired that the compression force on the disc stack is within a specific range for the brake torque to be within a specific range. By using a pre-compressed spring which is contacted and compressed a little further when engaging the brake, a relatively precise total spring compression may be achieved. Component tolerances (including a tolerance of a free length of the spring) may be relatively small in relation to the total compression of the spring. This may result in a consistent spring force and a robust brake system.

The endoscope control system can alternatively be denoted an endoscope bending operation apparatus.

The control system may be positioned on or in, or may form part, of an endoscope handle of the endoscope, see also further below.

One or more or all the brake discs may be rings circumscribing an axis of rotation of the control wheel. The rings may have a center opening through which a center shaft of the control system and/or other components, such as the spring may extend. The center opening may be relatively large compared to a diameter of the rings.

One or more of the first to third brake discs or further brake discs may be shaped as rings, i.e. as discs with a relatively small center opening.

One or more of the first to third brake discs or further brake discs may be split into disc or ring segments, such as two, three, or more segments. However, in this case, every second brake disc in the stack may not be split into such segments, i.e. may form a full ring. This may provide a multi-disc brake, where the disc segments or ring segments could be considered to form brake shoes acting on an adjacent, full-ring brake disc.

The control system may comprise a brake handle or a similar activation device or activation means, movement of which changes the multi-disc brake between the braking state and the released state. Such movement may be a rotation, potentially about a rotation axis of the control wheel. Movement of the brake handle may be transferred to the multi-disc brake by the brake handle rotating a rotation member, such as a disc, relative to a sliding member, such as a disc or one of the brake discs, the sliding member providing a pushing force on at least one of the brake discs activating the braking torque on the multi-disc brake. The rotation member and/or the sliding member may include an inclined portion or ramp so that rotating movement between the member along the inclined portion pushes the two members away from each other.

The brake handle may be positioned so that the brake handle does not touch the control wheel during the movement of the brake handle. The brake handle may comprise an arm that extends to the multi-disc brake.

Each of the brake discs may be formed in one piece or may include or be assembled from several pieces.

Every other of the brake discs of the stack may be connected or fixed to each other, and/or the remaining brake discs may similarly be connected or fixed to each other, these two sets of brake discs potentially being rotatable in relation to each other.

In the released state of the multi-disc brake, the springs(s) described further below may relieve or release frictional engagement of the brake discs and/or may push the brake discs out of frictional engagement.

All parts of the control system, potentially except for the spring(s) described below and/or steering wires and/or one or more of the brake discs may be manufactured from plastic polymer(s).

In some embodiments, the stack includes a first brake disc positioned between a second and a third brake disc of the stack, the first brake disc being rotatable in relation to the second and third brake discs, a first friction interface being provided between the first and second discs and a second friction interface being provided between the first and third brake discs, so that rotation of the first brake disc in relation to the second and third brake discs activates the first and second friction interfaces to provide at least part of the brake torque.

In embodiments where the control system comprises more than three, such as six or nine, brake discs, the entire stack or part of the stack of brake discs may be provided in a similar manner, i.e. so that such friction interfaces are provided between adjacent brake discs.

In some embodiments of the control system, a first of the brake discs is positioned between a second and a third of the brake discs so that the first brake disc has a first friction interface with the second brake disc and a second friction interface with the third brake disc, the first and second friction interfaces being activated in the braking state of the multi-disc brake and being at least partly released or deactivated in the released state of the multi-disc brake.

A set of discs, including e.g. the first third discs, may be stationary discs, and a set of discs, including e.g. the second disc, positioned in between may be rotating discs. The set of stationary discs may be fixed in relation to the frame or handle housing of the endoscope as described elsewhere herein. The set of rotating discs may be fixed in relation to a rotating part of the control system including the control wheel. These two different types of discs can be placed in any order, preferably alternating. Friction interfaces may be present where the two different types of brake discs interface.

The friction interfaces may include at least parts of two opposed major surfaces of the first brake disc, these major surfaces facing or abutting corresponding major surfaces of the second and third brake discs, the friction interfaces similarly potentially including at least part of these second and third brake disc major surfaces. If the stack includes more than three brake discs, the further brake discs may be arranged in a corresponding manner.

In a further development of the control system, when moving the multi disc brake from the released state to the braking state, a force is exerted on the stack of discs, the force pushing the second and third discs towards the first disc, the first and second friction interfaces thereby providing a brake force against rotation of the first brake disc relative to the second and third brake discs.

In another or further development, the control system further comprises a frame, the rotation of the control wheel occurring relative to the frame, and wherein the first brake disc is rotationally fixed relative to the control wheel, and the second and third brake discs are rotationally fixed relative to the frame.

The control wheel may be rotatable in relation to the frame. In embodiments where the control system comprises more than three brake discs, the brake discs may generally be arranged in the stack so that every other brake disc is rotationally fixed relative to the control wheel, and the remaining brake discs are rotationally fixed relative to the frame.

In a development of the latter embodiments of the control system, the frame is fixed to or forms part of an endoscope handle housing of an endoscope handle.

The handle housing may be a handle shell.

The frame and/or the housing may be manufactured of a rigid material, such as a rigid plastic polymer.

In some embodiments of the control system, the stack consists of six brake discs.

The stack may consist of three or more, four or more, five or more, six or more, seven or more, eight or more, nine or more, or ten or more brake discs.

In some embodiments of the control system, every other of the brake discs of the stack is manufactured from a material different from a material of the remaining brake discs.

Hereby, friction properties in the friction interfaces between associated or abutting brake discs may be controlled. In particular, by selecting suitable different materials, static friction may be lowered, which may improve control. For example, one material, such as polycarbonate (PC) or polypropylene (PP) may be selected for a first set of brake discs, and another material, such as acrylonitrile butadiene styrene (ABS), for the other set.

In some embodiments of the control system, at least one of the brake discs is manufactured from plastic polymer material.

Two or three or more or all brake discs may be manufactured from such material.

Especially if all brake discs are of such material, this may make the control system particularly suitable for disposable or one-use endoscopes.

The plastic polymer material may comprise or consist of one or more of PC, PP, ABS, polyethylene (PE), polyamide (PA), polyurethane (PU), polystyrene (PS), polylactic acid (PLA), polyvinyl chloride (PVC), polyoxymethylene (POM), polyester, polyethylene terephthalate (PET), and acrylic (PMMA). The polymer may be a copolymer of one or more monomers of the latter materials.

One or more of the brake discs may alternatively or additionally comprise or consist of a metal, such as steel, which may provide higher thermal conductivity. One of the abovementioned sets of brake discs may be of the plastic polymer material, and the other set of the metal.

Some embodiments of the control system further comprise a helical compression spring exerting a spring force on the stack of brake discs in the engaged state of the multi-disc brake.

The helical spring may be positioned coaxially with a center axis or center shaft of the control system or of the control wheel.

The helical spring may comprise or consist of metal, e.g. steel.

A spring characteristic of the helical spring can be made linear or substantially linear.

As alternatives to a helical spring, any other suitable spring may be used. The spring may be a diaphragm spring, cup spring, disc spring, saucer spring, or leaf spring. The spring or a spring function may be provided by or integrated in another component, such one of the brake discs, e.g. the first brake disc, or one set of brake discs being of a resilient material, such as a resin or a spring steel, and other discs or the other set of brake discs being of a substantially non-resilient material, such as (non-spring) steel. Alternatively, the spring is provided separately from the brake discs.

As alternatives to a compression spring, the spring may be a tension spring or a drive spring.

The control system may include two or more springs (for each control wheel, see further below), which may be helical and/or compression springs, or a combination of the above spring types may be used.

Instead of a spring, other means for activating the braking function of the stack of brake discs may be provided. Such other means could include an element, which can move a brake disc positioned at an end of the stack towards the other brake discs of the stack to provide the brake torque without providing a spring function. Such an element could be activated by a brake handle.

In a development of these embodiments, the spring is prestressed.

Advantages of a precompressed or prestressed spring may include that such a spring can provide a higher brake torque at smaller movements and/or that precise control can be provided at smaller movements. The necessary mechanical pressure can thus be achieved with a relatively limited movement of a brake handle. An advantage of such spring may be that compression of the spring in relation to a free length of the spring can be very precisely controlled by a small additional compression, resulting in a consistent spring force, thereby providing a more robust brake system. A small compression may require a small amount of energy, making it possible to engage the brake more easily by means of a brake handle.

In some embodiments, the control system further comprises: a further control wheel connected to a further wire drum for connection to a further steering wire of the endoscope, whereby rotation of the further control wheel controls the bending operation in another dimension than that of the control wheel; and a further multi-disc brake comprising a stack of at least three brake discs, wherein activation of the further multi-disc brake changes the further multi-disc brake from a released state to a braking state, a brake torque generated by the further multi-disc brake in the braking state braking rotation of the further control wheel, the brake torque in the released state being at least partially released.

The further control wheel and/or wire drum and/or steering wire and/or multi-disc brake may be embodied in accordance with any one of the above embodiments of the (first) control wheel, wire drum, steering wire, and multi-disc brake, respectively.

The further control wheel may be positioned coaxially with and potentially axially shifted in relation to the (first) control wheel. A diameter or a cross-sectional dimension of the two control wheels may be different from each other, potentially so that an outer one of the two control wheels has a smaller diameter or smaller cross-sectional dimension.

Alternatively, the further multi-disc brake may be replaced with a brake of another type.

In another aspect, the present disclosure involves an endoscope handle for an endoscope, the endoscope handle comprising a control system according to any one of above embodiments.

In another aspect, the present disclosure involves an endoscope comprising a control system according to any one of the above embodiments and/or an endoscope according to any one of the above embodiments.

The endoscope may further comprise an endoscope handle at the proximal end thereof, and/or visual inspection means, such as a built-in camera including a vision sensor, at a distal tip. Electrical wiring for the camera and other electronics, such as one or more LEDs accommodated in the tip part at the distal end, may run along the inside of the elongated insertion tube from the endoscope handle to a PCB or an FPC at the distal tip. A working or suction channel may run along the inside of the insertion tube from the handle to the tip part, e.g. allowing liquid to be removed from the body cavity or allowing for insertion of surgical and/or sampling instruments or the like into the body cavity. The suction channel may be connected to a suction connector, typically positioned at a handle at the proximal end of the insertion tube.

In some embodiments of the endoscope, the endoscope further comprises a distal tip or tip part that comprises a bending section connected to the steering wire(s) so that the control system can activate a bending operation of the bending section via the steering wire(s).

The bending section may be bendable in one or two dimensions, e.g. an up/down dimension and a left/right dimension. The bendable tip may comprise a bending section with increased flexibility, e.g. achieved by articulated segments of the bending section as are known in the art. The steering wire(s) may run along the inside of an elongated insertion tube from the tip through the bending section to the control system positioned in or forming part of the endoscope handle.

The endoscope may be a disposable insertion endoscope. The endoscope may include one or more features as described herein in the above, including the features of endoscopes described in the above introduction to this description, and in connection with the description of the methods and tip parts according to the present disclosure.

A second aspect of the present disclosure relates to a method of assembly of an endoscope control system, the endoscope control system being for performing a bending operation in a disposable insertion endoscope, wherein the endoscope control system comprises: a housing frame for forming or for forming part of an endoscope handle housing, the housing frame comprising a connection hole; a first control wheel unit comprising a first wheel handle; a second control wheel unit comprising a second wheel handle; a first shaft unit, the first shaft unit comprising a first wire drum and a first shaft, the first shaft connecting the first control wheel unit to the first wire drum, the first wire drum being for connection to a first steering wire of the endoscope, whereby rotation of the first wheel handle relative to the housing frame about an axis of rotation controls the bending operation in a first dimension; a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension; wherein the method of assembly comprises, in sequence, the steps of: 1) holding the first control wheel unit in a position; 2) moving the second control wheel unit in an assembly direction to position the second control wheel unit on the first control wheel unit; 3) moving the housing frame in the assembly direction to position the housing frame on the second control wheel unit; 4) moving the second shaft unit in the assembly direction so that the second shaft is positioned to extend through the connection hole of the housing frame and snaps into engagement with the second control wheel unit by means of a second snap connection between the second shaft and the second control wheel unit; and 5) moving the first shaft unit in the assembly direction so that the first shaft is positioned to extend through the connection hole of the housing frame and through the second shaft and snaps into engagement with the first control wheel unit by means of a first snap connection between the first shaft and the first control wheel unit; whereby the first and second control wheel units, the housing frame, and the first and second shaft units are maintained in position relative to each other in the assembly direction by means of the first and second snap connections.

In an embodiment according to the second aspect, the endoscope includes the multi-disk brake control system of the first aspect.

In a third aspect, the present disclosure involves an endoscope comprising the control system assembled according to the second aspect.

In an embodiment according to the third aspect, the endoscope includes the multi-disk brake control system of the first aspect.

In an embodiment according to the third aspect, the first control wheel is connected to the first wire drum for connection to a first steering wire of the endoscope, whereby rotation of the first control wheel relative to the handle housing about an axis of rotation controls the bending operation in a first dimension, the first control wheel comprising a bearing surface; the second control wheel is connected to a second wire drum for connection to a second steering wire of the endoscope, whereby rotation of the second control wheel relative to the handle housing about the axis of rotation controls the bending operation in a second dimension, the second control wheel comprising an outer bearing surface positioned farther from the axis of rotation than the bearing surface of the first control wheel; and an outer bearing element forming part of or being rotationally fixed to the handle housing, the outer bearing element comprising an inner bearing surface positioned farther from the axis of rotation than the outer bearing surface of the second control wheel, the inner bearing surface of the outer bearing element abutting the outer bearing surface of the second control wheel so that rotation of the second control wheel is at least partly borne on the outer bearing element.

In a fourth aspect of the present disclosure, an endoscope comprises: an endoscope handle with a handle housing; and endoscope control system. The endoscope control system comprises: a first control wheel connected to a first wire drum for connection to a first steering wire of the endoscope, whereby rotation of the first control wheel relative to the handle housing about an axis of rotation controls the bending operation in a first dimension, the first control wheel comprising a bearing surface; a second control wheel connected to a second wire drum for connection to a second steering wire of the endoscope, whereby rotation of the second control wheel relative to the handle housing about the axis of rotation controls the bending operation in a second dimension, the second control wheel comprising an outer bearing surface positioned farther from the axis of rotation than the bearing surface of the first control wheel; the first control wheel is connected to the first wire drum for connection to a first steering wire of the endoscope, whereby rotation of the first control wheel relative to the handle housing about an axis of rotation controls the bending operation in a first dimension, the first control wheel comprising a bearing surface; the second control wheel is connected to a second wire drum for connection to a second steering wire of the endoscope, whereby rotation of the second control wheel relative to the handle housing about the axis of rotation controls the bending operation in a second dimension, the second control wheel comprising an outer bearing surface positioned farther from the axis of rotation than the bearing surface of the first control wheel; and an outer bearing element forming part of or being rotationally fixed to the handle housing, the outer bearing element comprising an inner bearing surface positioned farther from the axis of rotation than the outer bearing surface of the second control wheel, the inner bearing surface of the outer bearing element abutting the outer bearing surface of the second control wheel so that rotation of the second control wheel is at least partly borne on the outer bearing element.

In an embodiment according to the fourth aspect, the endoscope includes the multi-disk brake control system of the first aspect.

The endoscope may comprise an elongated insertion tube with a handle at the proximal end. A tip or tip part may be positioned at the distal end of the elongated insertion tube. The tip may further comprise a bending section positioned between the tip and the elongated insertion tube. The bending section may be configured to be articulated to maneuver the endoscope inside a body cavity.

The endoscope may be a duodenoscope, a gastroscope, or a colonoscope.

A person skilled in the art will appreciate that any one or more of the above aspects of this disclosure and embodiments thereof may be combined with any one or more of the other aspects and embodiments thereof.

BRIEF DESCRIPTION OF THE DRAWINGS

In the following, non-limiting exemplary embodiments will be described in greater detail with reference to the drawings, in which.

DETAILED DESCRIPTION

In this disclosure, the term "to accommodate" may additionally or alternatively be defined as "to house" or "to enclose" or "to surround".

In this specification, the terms "integrally" or "integrally provided" or "integrally comprising", "in one piece" or similar may be defined as the associated features forming an integral part of a whole; and/or are in one piece, potentially molded in one piece; and/or are substantially inseparable by hand.

As mentioned, in this specification, the term "proximal" may be defined as being closest to an operator of the endoscope, and the term "distal" as being remote from the operator. The term "proximal-distal" may be defined as extending between these two extremes, in the present case proximal-distal may extend along a center axis of the tip part extending between a proximal extremity of the proximal end of the tip part and a distal extremity of the distal end of the tip part.

In this specification, an endoscope may be defined as a device adapted for viewing body cavities and/or channels of a human and/or animal body. The endoscope may for instance be a flexible or steerable endoscope. The endoscope may be a duodenoscope or a ureteroscope, a gastroscope, or a colonoscope.

Figure 1:
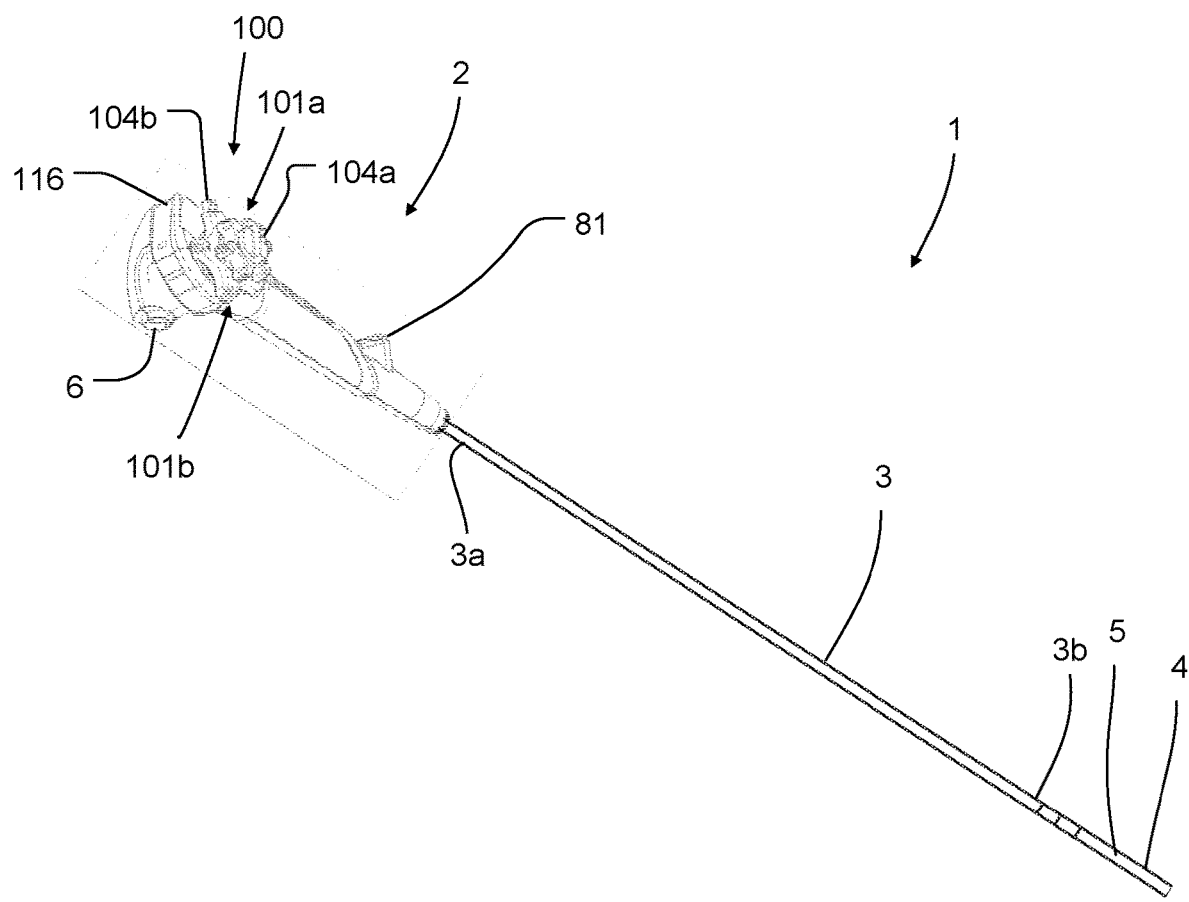
FIG. 1 shows a perspective view of an endoscope including a control system according to the present disclosure.
Figure 2:
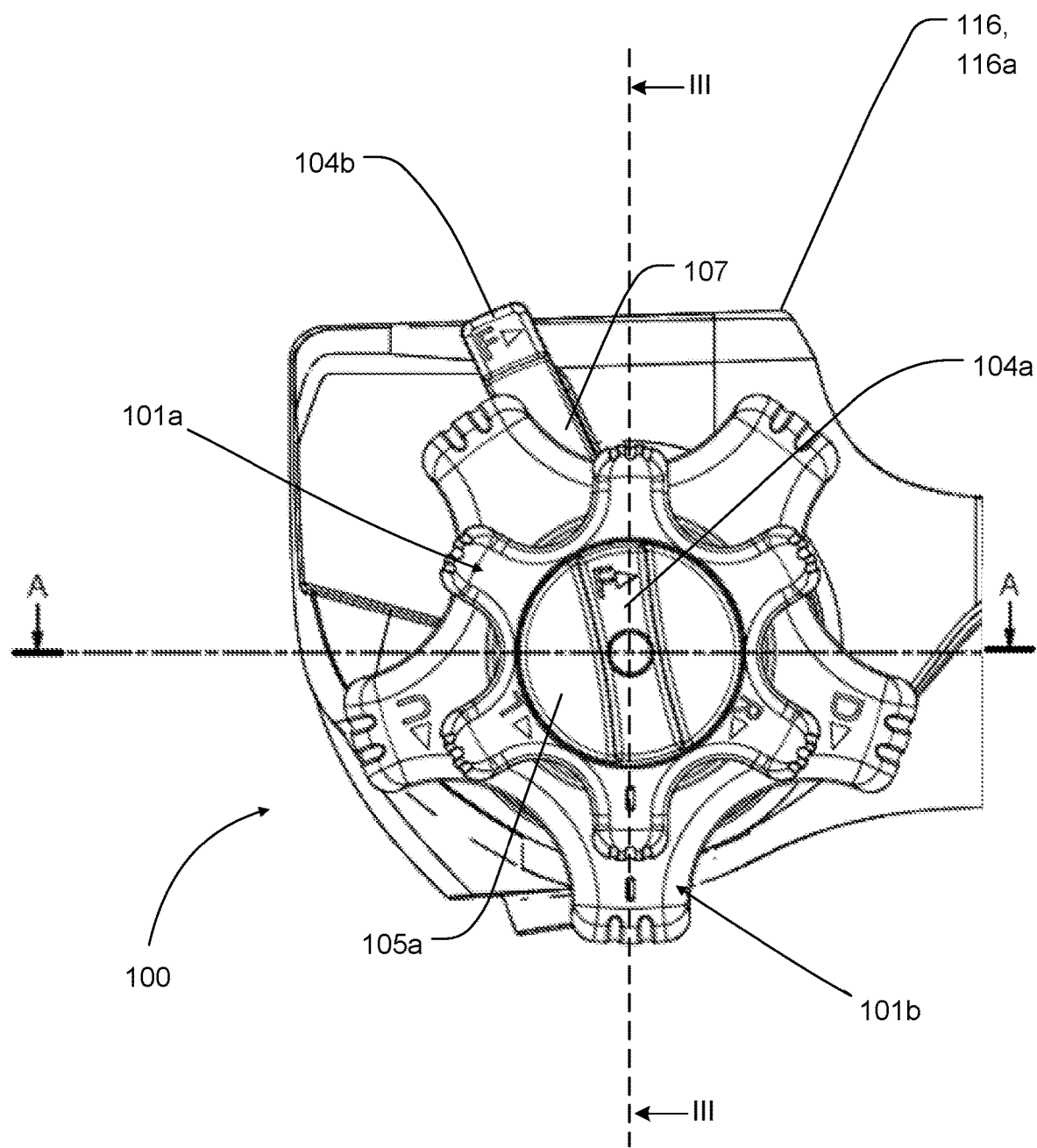
FIG. 2 shows a top view of the control system of FIG. 1.

FIG. 1 shows a perspective view of a disposable insertion endoscope 1 with a control system 100, an elongated insertion tube 3, and an endoscope handle 2 at a proximal end 3a of the elongated insertion tube 3. In a known manner, an endoscope tip 4 is positioned at a distal end 3b of the elongated insertion tube 3, the tip 4 comprising a bending section 5 positioned between the tip 4 and the elongated insertion tube 3. The endoscope handle 2 comprises the endoscope control system 100, the endoscope control system 100 being for performing a bending operation of the disposable insertion endoscope 1.

In a known manner, the bending section 5 is connected to steering wires, which extend from the control system 100 through the tube 3 to allow the control system 100 to activate a two-dimensional bending operation of the bending section 5 via the steering wires. The bending section 5 is configured to be articulated to maneuver the endoscope 1 inside a body cavity (not shown). The bending section 5 is bendable in two dimensions, i.e. an up/down dimension and a left/right dimension. In an alternative, not shown embodiment, the bending section is bendable in one dimension only. The bending section 5 has increased flexibility achieved by articulated segments of the bending section 5 as is known in the art. The steering wires run along the inside of the elongated insertion tube 3 from the tip 4 through the bending section 5 to the endoscope control system 100. Still in a known manner, the maneuvering of the endoscope 1 inside the body can be carried out by tensioning or slacking the steering wires by means of the control system 100.

Still in a known manner, the distal tip 4 has a not shown built-in camera including a vision sensor. Not shown electrical wiring for the camera and potential other electronics, such as one or more LEDs accommodated in the tip part 4, run along the inside of the elongated insertion tube 3 from the endoscope handle 2 to a PCB or an FPC at or in the distal tip 4. A not shown suction/working channel runs along the inside of the insertion tube 3 from the handle 2 to the tip part 4, e.g. allowing liquid to be removed from the body cavity or allowing for insertion of a surgical instrument and/or a sampling instrument or other instruments (not shown) into the body cavity. The suction channel is connected to a suction connector 6 positioned at the proximal end of the handle 2. A sampling connector 81 is positioned at the distal end of the handle 2.

The control system 100 comprises a first control wheel 101 and a second control wheel 102. Referring to FIGS. 1 to 7, the first control wheel includes a first control wheel unit 101a and a first shaft unit 102c coupled together (best seen in FIG. 6). Referring to FIGS. 8 to 10, the second control wheel includes a second control wheel unit 101b and a second shaft unit 102d coupled together (best seen in FIG. 10). Referring to FIGS. 11 to 15, control system 100 also comprises a first multi-disc brake 110a and, optionally, a second multi-disc brake 110b. The first and second multi-disk brakes 110a, 110b are also operable with control systems using different control wheels than those described with reference to FIGS. 1 to 14.

Figure 4:
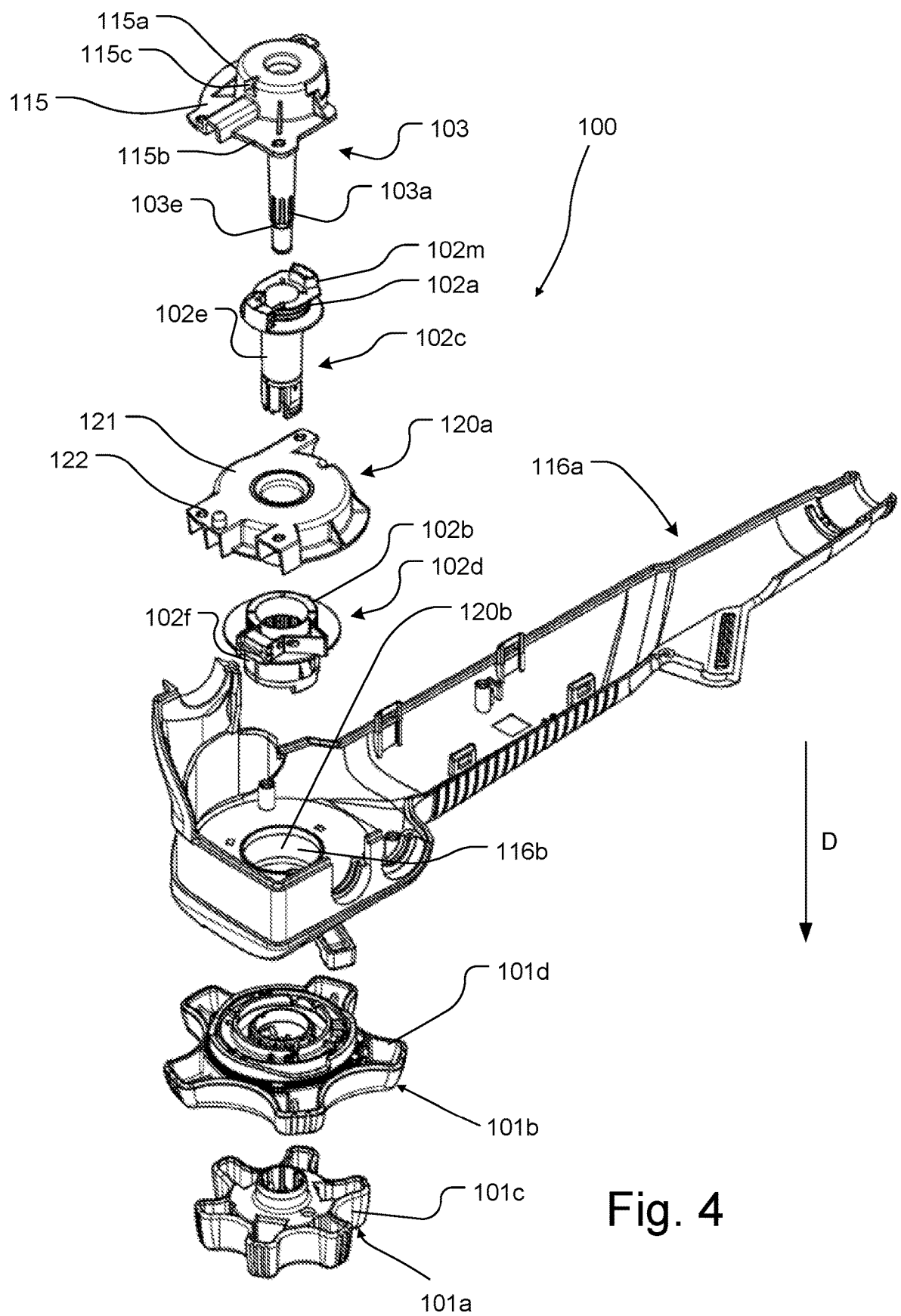
FIG. 4 shows an exploded perspective view of a handle frame and the control system of the endoscope of FIG. 1.

The endoscope control system 100 is shown exploded in FIG. 4 and comprises a housing frame 116a forming part of the handle housing 116 in the assembled endoscope 1, the housing frame 116a forming a half part of the assembled handle housing 116. The housing frame 116a at one end comprises a connection hole 116b.

The first control wheel 101 has a first wire drum 102a for connection to a steering wire of the endoscope 1, whereby rotation of the first control wheel 101 controls the bending operation by rotating the first wire drum 102a to, in a known manner, to activate a steering wire 102k (shown in FIG. 7), the steering wire being connected to the first wire drum 102a. The first control wheel unit 101a comprises a first wheel handle 101c comprising finger depressions. The second control wheel unit 101b comprises a second wheel handle 101d similarly comprising finger depressions.

The first shaft unit 102c comprises the first wire drum 102a and a first, sleeve-shaped shaft 102e, the first shaft 102e connecting the first control wheel unit 101a to the first wire drum 102a, the first wire drum 102a being for connection to a first steering wire 102k (shown in FIG. 7) of the endoscope 1, whereby rotation of the first wheel handle 101c relative to the housing frame 116a about an axis of rotation controls the bending operation in a first dimension. The second shaft unit 102d comprises a second wire drum 102b and a second shaft 102f, the second shaft 102f connecting the second control wheel unit 101b to the second wire drum 102b, the second wire drum 102b being for connection to a second steering wire (not shown)102l (shown in FIG. 10) of the endoscope 1, whereby rotation of the second wheel handle 101d relative to the housing frame 116a about an axis of rotation controls the bending operation in a second dimension.

Referring to FIGS. 4 to 10, an embodiment of the methods of assembly of the control system 100 according to the present disclosure comprises: 1) holding the first control wheel unit 101a in a fixed position; 2) moving the second control wheel unit 101b in an assembly direction D to position the second control wheel unit 101b on the first control wheel unit 101a; 3) moving the housing frame 116a in the assembly direction D to position the housing frame 116a on the second control wheel unit 101b; 4) moving the second shaft unit 102d in the assembly direction D so that the second shaft is positioned to extend through the connection hole 116b of the housing frame 116a and snaps into engagement with the second control wheel unit 101b by means of a second snap connection 113 (shown in FIGS. 8-10) between the second shaft 102f and the second control wheel unit 101b; and 5) moving the first shaft unit 102c in the assembly direction D so that the first shaft 102e is positioned to extend through the connection hole 116b of the housing frame 116a and through the second shaft 102f and snaps into engagement with the first control wheel unit 101a by means of a first snap connection 112 (shown in FIGS. 5-7) between the first shaft 102e and the first control wheel unit 101a; whereby the first and second control wheel units 101a, 101b, the housing frame 116a, and the first and second shaft units 102c, 102d are maintained in position relative to each other in the assembly direction D by means of the first and second snap connections 112, 113. These steps may be performed in sequence.

This method allows for mounting and positioning all the parts involved, i.e. the first and second control wheel units 101a, 101b, the housing frame 116a, and the first and second shaft units 102c, 102d from one side only and in the assembly direction D only. In each of the steps 2) to 5), only the next part to be added is moved in the assembly direction while the already assembled parts are not moved. Mounting and positioning all the parts involved from one side only simplifies assembly and such simplification and corresponding manufacturing cost reduction is made possible by the present embodiment. As described below, a jig could be used to assemble the parts in sequence. While the method may be performed with the steps 1) to 5) performed in sequence, the first and second control wheel units 101a, 102b could be mated before placing them onto the jig, and the first and second shaft units 102c, 102d could be assembled together before snapping the shafts onto the first and second control wheel units 101a, 102b. In another example, the first and second shaft units 102c, 102d and the housing frame 116a could be assembled together before snapping the shafts onto the first and second control wheel units 101a, 102b. In a further example, a jig could be used to assemble the system from the opposite direction, mounting the shafts on the jig and then, in the direction opposite D, snapping the first and second control wheel units 101a, 102b onto the first and second shaft units 102c, 102d. As can be deduced from the foregoing, the assembly advantages are derived from the structures of the components being assembled. The assembly direction D may be referred to as the axial direction.

The first control wheel unit, the second control wheel unit, the housing frame, the second shaft unit and the first shaft unit can be considered components of a stack, and the method can thus comprise stacking the components in order to form the stack. Stacking the components in order comprises holding a portion of the stack while moving the components onto the portion of the stack being held. The first control wheel unit can be considered part of the stack and can be held in the jig, as described, as the other components are stacked via movement in the axial direction toward the first control wheel unit. The stack may comprise an inner bearing element frame and a center shaft. The method may include, after moving the second shaft unit, moving the inner bearing element frame in the axial direction to position the inner bearing element frame through the connection hole of the housing frame. The inner bearing element frame has a portion positioned between the first shaft and the second shaft. The method may include, after moving the first shaft unit, moving a center shaft in the axial direction to position the center shaft through the first shaft and moving a cap in the axial direction toward the first control wheel unit to form a snap connection between a tip end of the center shaft and the cap to secure the center shaft in place.

The method can comprise stacking the first multi-disc brake 110a and, optionally, the second multi-disc brake 110b. The first multi-disc brake 110a may be stacked after assembly of the first and second control wheels 101, 102, and the second multi-disc brake 110b may be stacked after stacking the second control wheel unit prior to stacking the frame, as is evident from FIG. 15.

Figure 11:
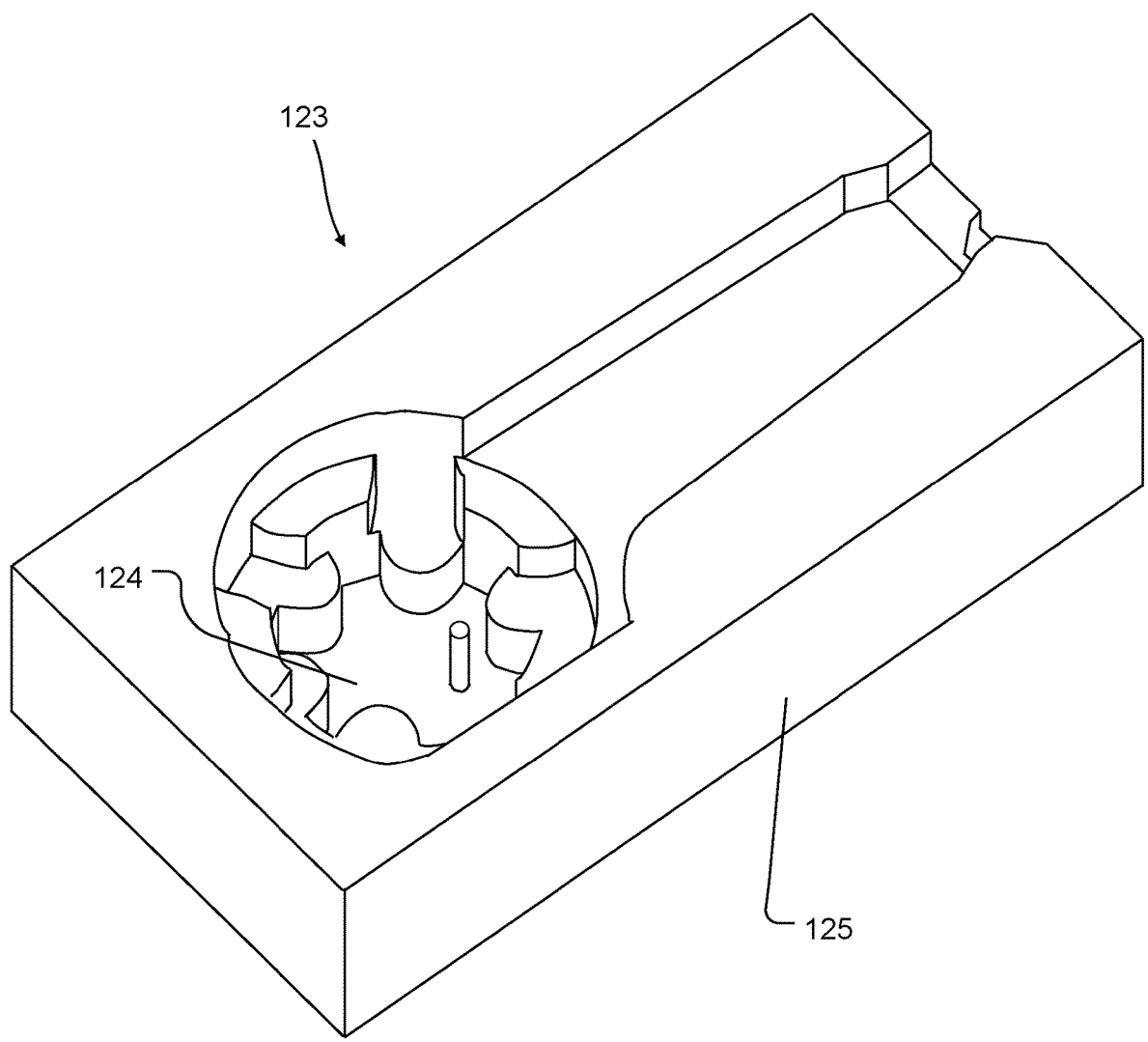
FIG. 11 shows a perspective view of a jig.

The first and second snap connections 112, 113 ensure that the parts of the control system assembled in steps 1) to 5) are attached to each other only by means of the movement carried out in steps 4) and 5). Accordingly, the movement in each of steps 4) and 5) activate the snap connections 112, 113 without any further action being required to activate these. No locking rings or separate locking elements are applied during or between steps 1) to 5). Flipping around or turning the already assembled parts is avoided during the sequence of steps 1) to 5). A jig 123 as shown in FIG. 11 and is used as described below during the method steps 1) to 5), and the already assembled parts are do not need to be removed from the jig 123 during steps 1) to 5).

The housing frame 116a is a first half shell of the handle housing 116a, the handle housing 116a further comprising a second half shell that is attached to the first half shell 116a after completion of steps 1) to 5). Hereby, the first and second wire drums 102a, 102b are positioned inside the assembled handle housing 116.

The first and second wheel handles 101c, 101d are generally circular and/or comprise conventionally provided finger depressions or cut-outs.

Figure 5:
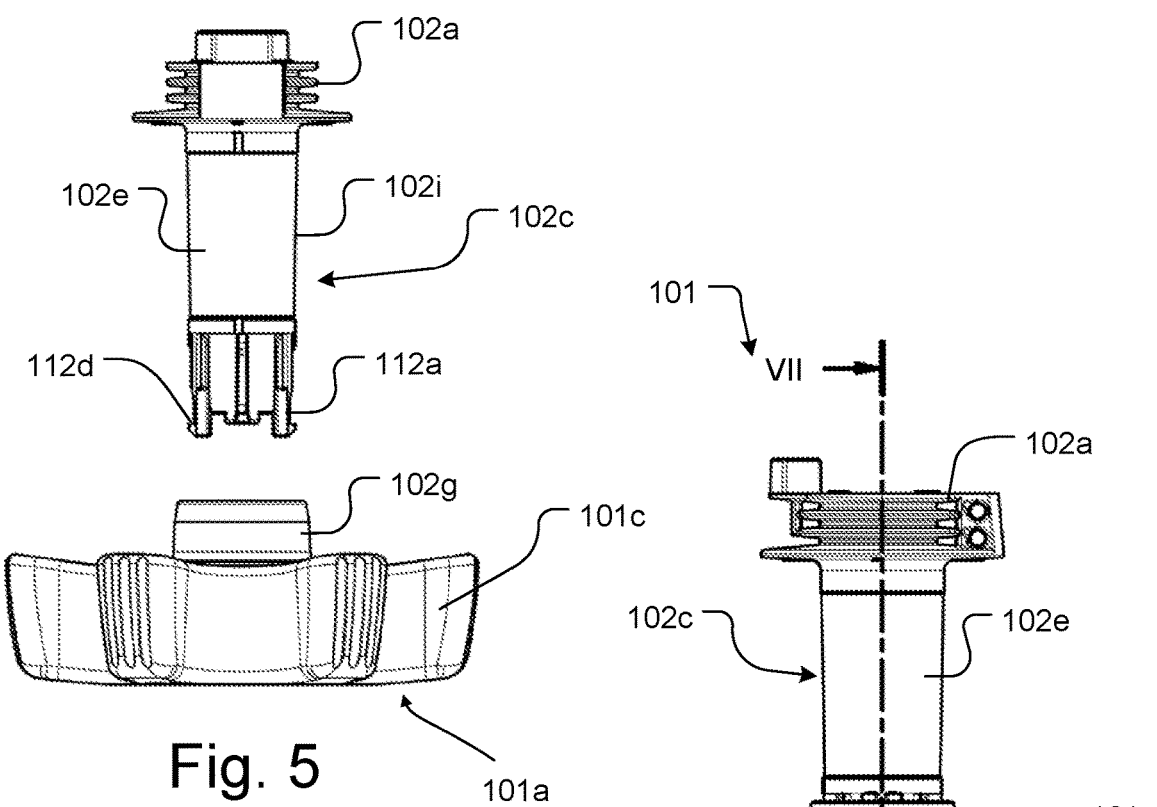
FIG. 5 shows an exploded side view of a first control wheel of the control system of FIG. 1 including a first control wheel unit and a first shaft unit.
Figure 6:
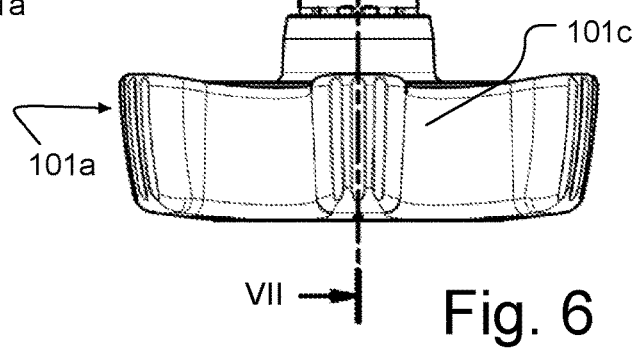
FIG. 6 shows an exploded side view of the first control wheel of FIG. 5 in an assembled state and turned 180 degrees.
Figure 7:
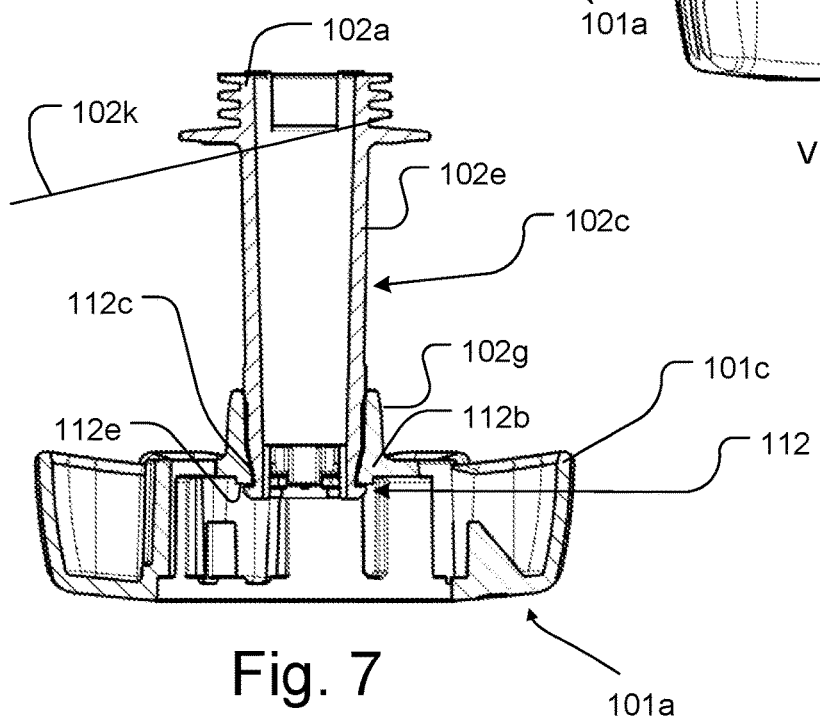
FIG. 7 shows a cross section taken along the line VII-VII in FIG. 6.
Figure 8:
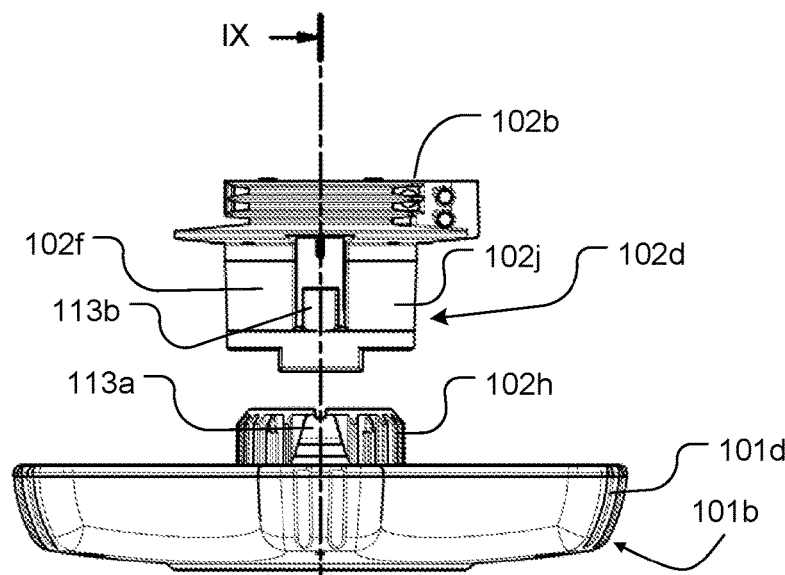
FIG. 8 shows an exploded side view of a second control wheel of the control system of FIG. 1 including a second control wheel unit and a second shaft unit.
Figure 9:
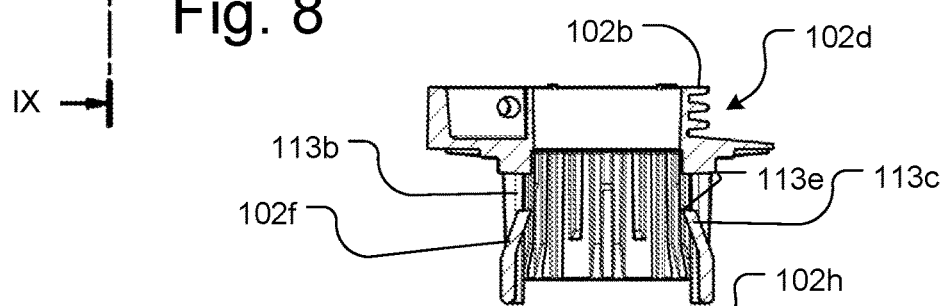
FIG. 9 shows a cross-sectional view taken along the line IX-IX of FIG. 8.
Figure 10:
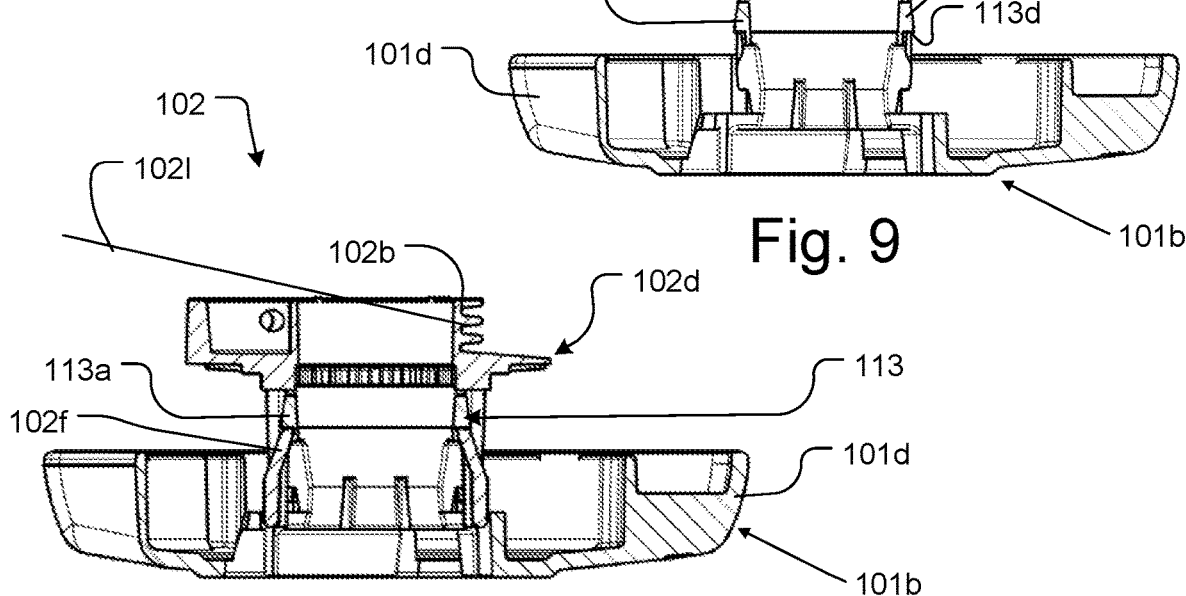
FIG. 10 shows a view like that of FIG. 9, wherein the second control wheel unit and second shaft unit are in an assembled state.

FIGS. 5-7 describe the components of and the first snap connection 112, and FIGS. 8-10 describe the components of and the second snap connection 113. Each of the first and second control wheel units 101a, 101b comprises a central part or wheel sleeve 102g, 102h, first and second, respectively, each surrounding a center opening. The central parts 102g, 102h are cylindrical and extend towards the housing frame 106a in the assembled control system 100. In the assembled control system 100, the second central part 102h may in other embodiments extend to encompass part of the first central part 102g in the assembled state of the control system 100.

The first shaft 102e comprises a bearing surface 102i, and the second shaft 102f comprises a bearing surface 102j, the bearing surfaces 102i, 102j being for abutment and rotational sliding on associated bearing elements fixed to the housing frame 116a, see further below.

The first and second shafts 102e, 102f are each tubular and each comprises a substantially cylindrical circumferential wall which provide the associated bearing surfaces 102i, 102j. A diameter of the first shaft 102e is smaller than that of the second shaft 102f.

The axes of rotation of the control wheel units 101a, 101b are coinciding to form one axis of rotation, which is also a center axis of the control system 100. This axis extends in the assembly direction D. The first and second shafts 102e, 102f, the first and second control wheel units 101a, 101b, and the first and second wheel handles 101c, 101d extend coaxially in the assembled control system 100.

In the assembled control system 100, as shown in FIG. 4, the first and second wire drums 102a, 102b on the one hand and the first and second wheel handles 101c, 101d on the other hand are positioned on opposite sides of the connection hole 116b of the housing frame 116a. The first wire drum 102a is positioned in extension of the second wire drum 102b and farther from the housing frame 116a or the connection hole 116b than the second wire drum 102b.

The first and second wire drums 102a, 102b are positioned at upper ends of the first and second shafts 102e, 102f, respectively.

The assembled control system 100 further includes an inner bearing element 120a which in a further step after step 4) is moved in the assembly direction D to extend through the second shaft unit 102d and through the connection hole 116b of the housing frame 116a. In the assembled control system 100, the inner bearing element 120a is rotationally fixed to the housing frame 116a. The inner bearing element 120a comprises an inner bearing surface 120c (FIG. 3) positioned farther from the common axis of rotation than the outer bearing surface 102i of the first shaft 102e, the inner bearing surface 120c abutting the outer bearing surface 102i so that rotation of the second control wheel unit 101b is at least partly borne on the inner bearing element 120a. The inner bearing element 120a includes a cylindrical, tubular inner bearing sleeve having a wall. The inner bearing element 120a separates rotation of the control wheel units 101a, 101b from each other.

The assembled control system further comprises an outer bearing element 120b in one piece with the housing frame 116a. The outer bearing element 120b surrounds and defines the connection hole 116b of the housing frame 116a. The outer bearing element 120b is tubular and cylindrical and comprises a wall which extends away from the housing frame 116a in a direction towards the first control wheel unit 101a. The outer bearing element 120b comprises an inner bearing surface 120d (FIG. 3) positioned farther from the common axis of rotation than the outer bearing surface 102j of the second shaft 102f, the inner bearing surface 102j abutting the outer bearing surface 102j so that rotation of the second control wheel unit 101b is at least partly borne on the outer bearing element 120b. The outer bearing element 120b is an outer bearing sleeve that encompasses at least part of the second shaft 102e.

The control system 100 further includes a center shaft 103 which, in a further step after step 5), is moved in the assembly direction D to extend through the connection hole 116b of the housing frame 116a, the first and second shaft units 102c, 102d, and the center openings of the first and second control wheel units 101a, 101b. The center shaft 103 comprises a connector frame or center shaft frame 115, and the connector frame 115 is fixed by means of pins (not shown) to the housing frame 116a via the inner bearing element frame 121, see below, after insertion of the center shaft 103 so that the center shaft 103 is fixed to the housing frame 116a (not shown). The connector frame 115 extends radially from a shaft part 103a of the center shaft 103 and is positioned within the handle housing 116a in the assembled endoscope 1, see FIG. 3. The connector frame 115 includes a housing 115a including a flange 115b fixed to the housing frame. The housing 115a includes an indentation 115c that operates as stop or stop surface when it contacts a corresponding stop surface 102m on a longitudinally protruding portion of the first shaft unit 102c as it rotates. The protruding portion has an arcuate shape and its length determines the angle of rotation of the first shaft unit 102c.

Similarly, the inner bearing element 120a includes an inner bearing element frame 121 that extends radially from a sleeve part 120e thereof and is positioned within the handle housing 116 in the assembled endoscope 1. The inner bearing element frame 121 is directly fixed to the housing frame 116a, the center shaft frame 115 being directly fixed to the inner bearing element frame 121 by means of screws (not shown) so as to be indirectly fixed to the housing frame 116a. The screws are inserted into screw holes, one of these being designated 122 in FIG. 4.

The first and second shafts/sleeves are each cylindrical or, rather, slightly conical, and hollow. The second shaft/sleeve 102f encompasses a part of the first shaft/sleeve 102e. The outer bearing element 120b encompasses part of the second shaft/sleeve 102f. The inner bearing element 120a comprises an inner bearing sleeve or sleeve part 120e that encompasses part of the first shaft/sleeve 102e. The outer bearing element encompasses part of the second shaft/sleeve 102f, which again encompasses part of the sleeve part 120e, which again encompasses part of the first shaft/sleeve 102e.

The second shaft/sleeve 102f is positioned between and is rotational relative to the inner and outer bearing elements 120a, 120b, which are static relative to the handle housing 116, the second shaft/sleeve 102f being rotationally borne or supported on the outer bearing element 120b. The first shaft/sleeve 102e is positioned on an interior side of the inner bearing element 120a and is rotational relative to the inner and outer bearing elements 120a, 120b, which are both static relative to the handle housing 116.

The inner bearing element 120a separates the first and second control wheels 101, 102 from each other so that rotation is mutually separated.

The first shaft/sleeve 102e embodies the first wheel sleeve mentioned above, and the second shaft/sleeve 102f embodies the second wheel sleeve mentioned above.

The first and second wire drums 102a, 102b are positioned inside the assembled handle housing 116.

The first and second wheel handles 101c, 101d are generally circular and comprise conventionally provided finger depressions or cut-outs.

Each of the first and second control wheels 101, 102 comprises a central part 102g, 102h, first and second, respectively, each surrounding a center opening. The central parts 102g, 102h are cylindrical and extend towards the housing frame 106a. The second central part 102h may in other embodiments extend to encompass part of the first central part 102g in the assembled state of the control system 100.

The first and second shafts 102e, 102f are each tubular and each comprises a substantially cylindrical or, rather, slightly conical circumferential wall which provide the associated bearing surfaces 102i, 102j. A diameter of the first shaft 102e is smaller than that of the second shaft 102f.

When the center shaft 103 has been positioned, a cap 105a is moved opposite to the assembly direction D to be attached to a tip end 103b of the center shaft 103 by a snap connection 103c which is provided in a manner similar to the first and second snap connections 112, 113. Accordingly, the cap 105a includes two resilient and pushable connection parts 103d, whereas the tip end 103b includes associated two connection parts taking the form of recesses 103e. This snap engagement 103c is similarly be activated during or at the end of the insertion of the center shaft 103 into the control system 100. The cap 105a covers and attaches the first multi-disc brake 110a of the first control wheel unit 101a, see further below. The brake 110a is encased within a spacing defined by interior surfaces of the first wheel handle 101c. Before insertion of the brake 110a and subsequent positioning of the cap 105a, i.e. after steps 1) to 5), the assembled parts of the control system 100 are removed from the jig 123 and the assembled parts of the control system 100 are flipped around, i.e. turned 180 degrees, after which the first brake 110a is assembled and positioned to form part of the first control wheel unit 101a, after which, again, the cap 105a is positioned as described. Alternatively, the brake 110a and the cap 105a are mounted to form part of the first control wheel unit 101a before or during step 1). The cap 105a includes a brake knob 104a projecting in the assembly direction and upon rotation of which the brake 110a is activated to brake rotation of the first control wheel unit 101a and, thus, first shaft unit 102d.

The inner bearing surface 120d and the outer bearing surface 102j each includes two circumferentially extending bearing surface parts or bearing interfaces, which are positioned at an axial distance from each other. In these interfaces, the surfaces 120d and 102j are in abutment with each other. Hereby, stability of the rotational movement is provided. The bearing surface parts are positioned at upper and lower parts or ends of the second shaft/sleeve 102e and the outer bearing element/sleeve 120b. Similarly, the inner bearing surface 120c of the inner bearing element 120a and the outer bearing surface 102i of the first control wheel 101 each includes two bearing surface parts, which are similarly positioned at an axial distance from each other.

In the assembled control system 100, a brake handle 104b for activation of a similar, second multi-disc brake 110b, which brakes the second control wheel unit 101b in a similar manner, is attached to the housing frame 116a. During the method of assembly, when the second control wheel unit 101b has been positioned in step 2), before step 3), the brake handle 104b is moved in the assembly direction to be positioned on the second control wheel unit 101b.

In step 1), the first control wheel unit is positioned in and at the bottom of a correspondingly shaped part of a jig depression 124 of the jig 123 shown in FIG. 11, the jig 123 holding the first control wheel unit 101a in a fixed position. In step 2), the second control wheel unit is also positioned and held in a correspondingly shaped part of the jig depression 124. In step 3), the housing frame is also positioned and held in a correspondingly shaped part of the jig depression 124. The jig 123 includes a jig block 125 with in which the jig depression 123 is shaped to provide a positive engagement with the first control wheel unit 101a, especially the first wheel handle 101c. Similarly, the jig depression 124 is shaped to also provide a positive engagement with the second control wheel unit 101b, especially the second wheel handle 101d, when the second control wheel unit 101b is positioned on the first control wheel unit 101a in the jig 123. Similarly, the jig depression 124 is shaped to also provide a positive engagement with the housing frame 116a when the housing frame 116a is positioned on the second control wheel unit 101b in the jig 123. Hereby, all of these elements can be maintained in relative positions until the snap connections 112, 113 are engaged in steps 4) and 5).

After steps 1) to 5), the assembled control system 100 is removed from the jig 123, and further assembly occur as described. This involves assembly of the handle housing 116.

Referring to FIGS. 8 to 10, the second snap connection 113 axially and rotationally fixes the second shaft unit 102d to the second control wheel unit 101b. The second snap connection 1032d includes two connection parts 113a in the form of resilient projections or pins of the second control wheel unit 101b shaft unit 102d which interlock with two associated connection parts 113b, embodied by recesses, of the second shaft unit 102d control wheel unit 101b. These connection parts 113a, 113b are thus mutually engaging. During the movement of the second shaft unit 102d, the connection parts 113a are pushed in a radial direction (inwardly) and, then, when the second shaft unit 102d is further moved or inserted, resiliently snap back to engage with the associated connection parts 113b. The connection parts 113b includes a ramp or inclined surface 113c, which forces the pushable connection parts 113a inwardly in a radial direction during the movement of the second shaft unit 102d. Accordingly, the pushable connection parts 113a include a barb surface 113d which during the snap moves into engagement with an associated barb surface 113e of the other connection parts 113b to secure the position of the second shaft unit 102d to the second control wheel unit 101b. The pushable connection parts 113a are included in the second central part 102h, and the associated connection parts 113b are included in the second shaft unit 102d. The pushable connection parts 103a may each be provided by two axially extending slots defining a resilient, axially moveable pin between them, as in conventional snap fittings.

As described, the second snap connection 113 includes a barb surface 113d which during the snap moves into engagement with an associated barb surface 113e to secure the position of the second shaft unit 102d relative to the second control wheel unit 101b. As shown, opposed walls, each comprising an inwardly projecting angled portion extending from a vertical portion below it, are provided on the second shaft unit 102d. Each of the inwardly projecting angled portions includes an inclined surface 113c and ends a the barb surface 113e. In alternative embodiments, the inwardly projecting angled portion can be resilient and the connection parts 113a can be of various rigidities, since the inwardly projecting angled portions can flex outwardly to allow the two connection parts 113a to move past them into the cavities 113b. Thus, the second snap connection 113 is made by opposing barb surfaces, at least one of which is provided by a radially resilient part.

Referring to FIGS. 5 to 7, like the second snap connection 113, the first snap connection 112 axially and rotationally fixes the first shaft unit 102c to the first control wheel unit 101a. And the first snap connection 112 includes two connection parts 112a of the first shaft unit 102c interlocking with two associated connection parts 112b (best seen in FIG. 7) of the first control wheel unit 101a. These associated connection parts 112a, 112b mutually engage. During the movement of the first shaft unit 102c, the connection parts 112a are pushed inwardly in the radial direction by the wheel sleeve 102g and, then, when the first shaft unit 102c is further moved and inserted, resiliently snap back to engage the associated connection part 112b. And again, this is achieved by the connection parts 112b including a ramp or inclined surface 112c, which forces the pushable connection parts 112a in the radial direction during the movement of the first shaft unit 102c. Accordingly, the pushable connection parts 112a include a barb surface 112d which during the snap moves into engagement with an associated, opposed barb surface 112e of the connection parts 112b to secure the position of the first shaft unit 102c to the first control wheel unit 101a. The pushable connection parts 112a are included in the first shaft unit 102c, in the first shaft 102e thereof, and the associated connection parts 112b are included in the first control wheel unit 101a. The pushable connection parts 112a may be provided by two axially extending slots defining a resilient, axially moveable pin between them.

As described, the first snap connection 112 includes a barb surface 112d which during the snap moves into engagement with an associated barb surface 112e to secure the position of the first unit 102c relative to the second control wheel unit 101a. In alternative embodiments, the connection parts 112b do not need to include a ramp or inclined surface 112c. The pushable connection parts 112a each includes a ramp or inclined surface at the distal end thereof, which can force the pushable connection parts 112a inwardly in the radial direction during the movement of the first shaft unit 102c when the ramps contact the inner surface of the wheel sleeve 102g. Thus, the first snap connection 112 is made by opposing barb surfaces, at least one of which is provided by a radially resilient part.

Hereby, the first and second snap connections 112, 113, when engaged, prevent movement of the first and second control wheels 101a, 101b, the housing frame 116a, and the first and second shaft units 102c, 102d relative to each other in the assembly direction D. Accordingly, the barb surfaces 112d, 112e; 113d, 113e face in the axial direction and are mutually opposed to each other during and after assembly. Barbs of the connection parts 112a, 113a are provided as projections extending in the radial direction.

The assembly direction D is parallel with the axes of rotation of the first and second control wheel units 101a, 101b.

Figure 3:
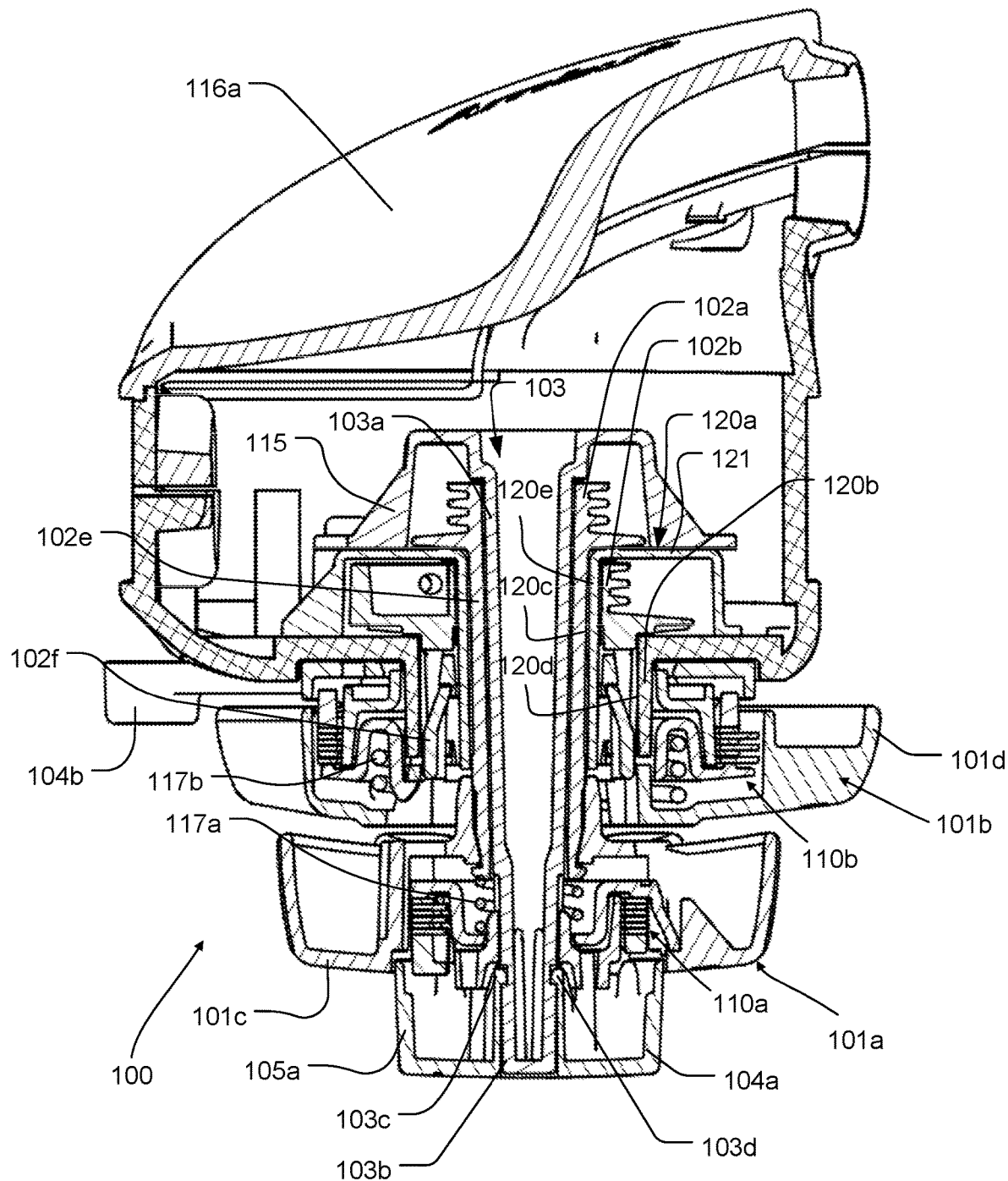
FIG. 3 shows a cross-sectional view taken along line III-III in FIG. 2.

As shown in FIG. 3, in the assembled control system 100, the first and second control wheel units 101a, 101b house the associated brakes 110a, 110b. Activation of each of the brakes 110a, 110b moves the brake from a released position to a braking position. A brake force of the brake 110a, 110b in the braking position brakes rotation of the associated control wheel unit 101a, 101b, respectively. The brake force is released in the released position. The brake 110b is assembled in the second wheel handle before step 1). The brakes 110a, 110b each includes a stack of brake discs and a helical spring 117a, 117b, respectively.

After assembly of the control system 100 and then the handle 2, the control system 100 forms part of the handle 2.

Rotation of the control wheel units 101a, 10b occurs relative to the housing frame 116a during the bending operation.

The handle housing 116 takes the form of a housing shell.

The first and/or second wire drums 102a, 102b are pulleys. In the assembled endoscope 1, the not shown first and second steering wires are attached to the wire drums 102a, 102b to be woundable on these, respectively.

Any one or more of or all steps 1) to 5) can be carried out manually and/or automatically. Any one or more or all of the further steps of assembly may also be carried out manually and/or automatically.

In each of steps 2) to 5), all already positioned parts of the control system 100 remain in the held position.

The snap connection parts 112a, 112b; 113b, 113a are provided in one piece with the first shaft unit 102c and the first control wheel unit 101a; the second shaft unit 102d and the second control wheel unit 101b, respectively.

Figure 12:
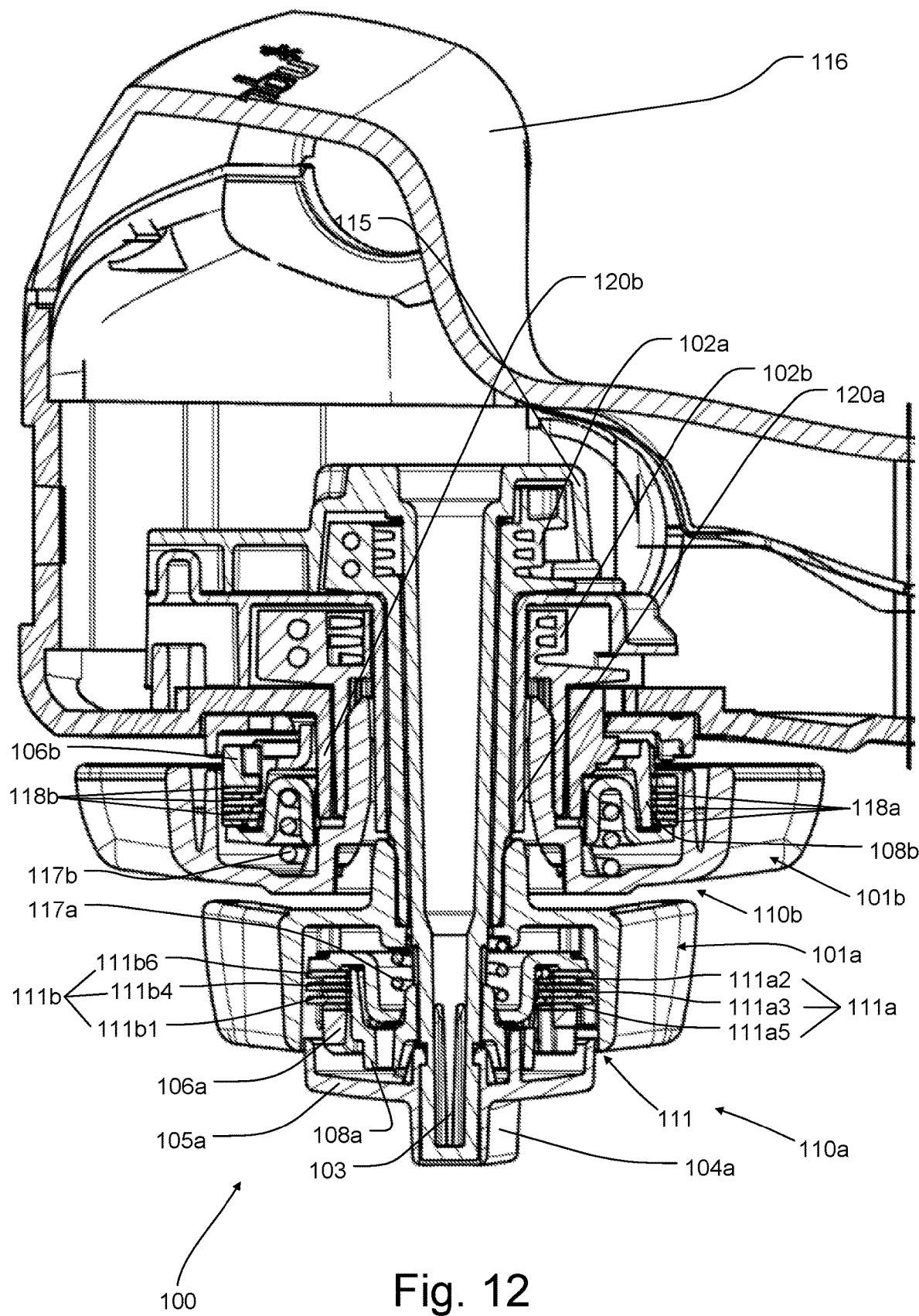
FIG. 12 shows a cross-sectional view taken along line A-A in FIG. 2.
Figure 13:
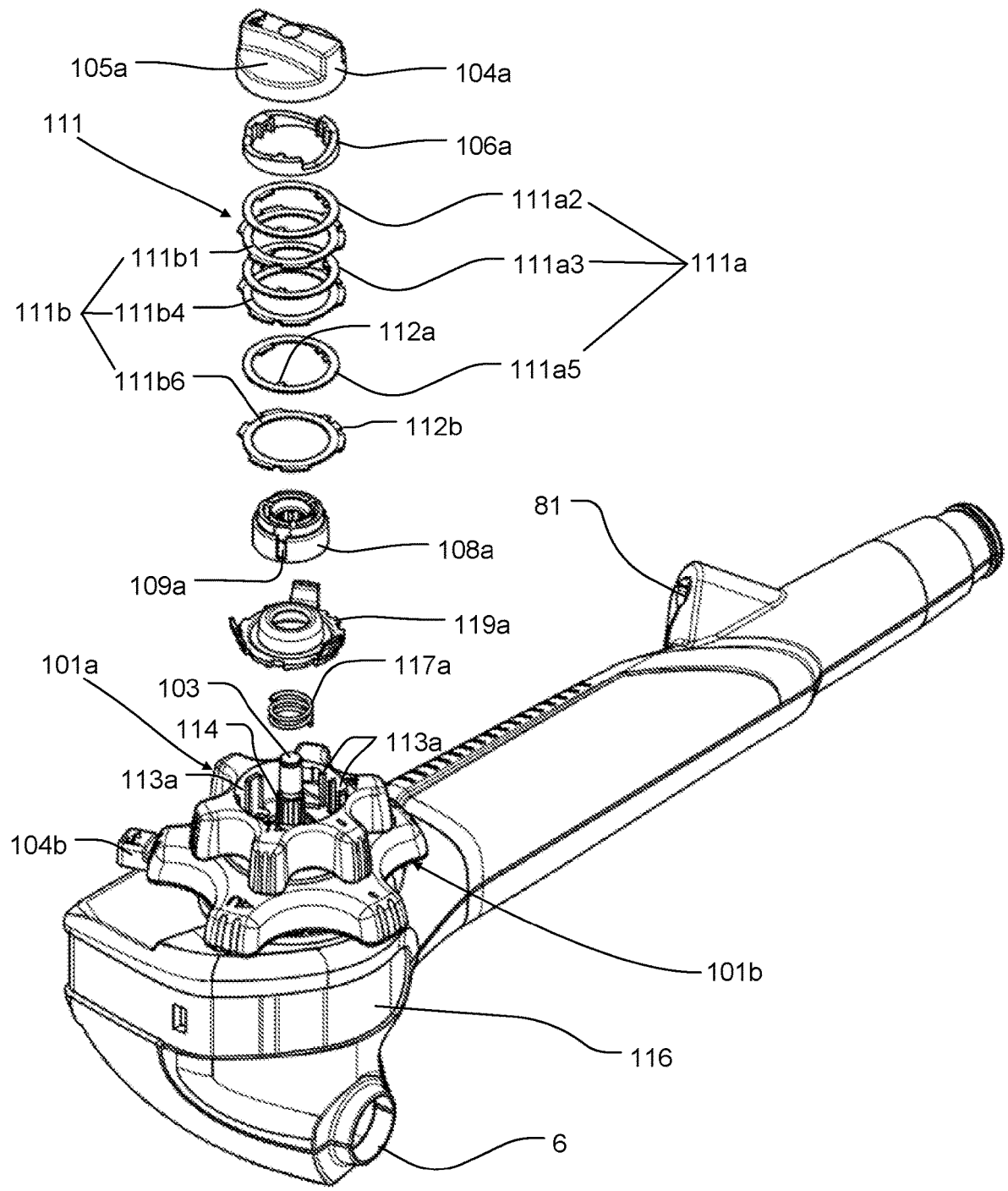
FIG. 13 shows a perspective view of a handle of the endoscope of FIG. 1, a first multi-disc brake of the first control wheel of the control system being shown in an exploded view.

Referring to FIGS. 12 to 15, the control system 100 comprises the first multi-disc brake 110a comprising a stack 111 of two brake disc sets 111a, 111b, see e.g. FIG. 13. Activation of the brake 110a changes the multi-disc brake 110a from a released state to a braking state. In the braking state, a brake torque generated by the brake 110a brakes rotation of the first control wheel 101, the brake torque being released in the released state. The brake 110a makes it possible to control the braking torque (in the braking state). The brake 110a is designed so that the braking torque is high enough to leave the tip 4 of the endoscope 1 in a desired bent or unbent position, but not so high as to risk injury to or damaged tissue of a patient, e.g. if the physician by mistake should attempt to retract the tip 4 from the patient without releasing the brake 110a.

The brake discs shown at 111a and 111b are shaped as rings circumscribing an axis of rotation of the first control wheel 101. The ring-shaped brake discs shown at 111a and 111b have a center opening through which a center shaft 103 of the control system 100 extends. The center opening is of relatively large diameter compared to a total diameter of the rings.

The control system 100 further comprises an activation device in the form of a brake knob 104a, rotation of the brake knob 104a about a rotation axis of the first control wheel 101 moving the brake 110a between the braking state and the released state. Movement of the brake knob 104a rotates a disc-shaped rotation member 105a thereof relative to a disc-shaped sliding member 106a. In the braking state, the sliding member 106a activates an axial force pushing the brake discs at 111a, 111b towards each other to activate the braking torque of the brake 110a. The rotation member 105a and the sliding member 106a include interacting inclined portions so that mutual rotation along the inclined portions in a per se known manner pushes the rotation member 105a and the sliding member 106a away from each other, i.e. the sliding member 106a is pushed towards the brake 110a to activate the break 110a as will be described further below.

As best seen in FIG. 13, each of the brake discs at 111a, 111b is formed in one piece, every other of the brake discs, i.e. the brake discs at 111a, are connected to each other by a disc holder 108a, where disc protrusions 112a engage disc holder grooves 109a. The remaining brake discs at 111b are similarly connected to each other by the first control wheel 101, disc protrusions 112b of the brake discs 111b engaging control wheel grooves 113a, so that the two sets 111a, 111b of brake discs are rotatable in relation to each other.

The set 111b includes a first brake disc 111b1 positioned between a second and a third brake disc 111a2, 111a3 of the set 111a, the first brake disc 111b1 being rotatable in relation to the second and third brake discs 111a2, 111a3, a first friction interface being provided between the first and second brake discs 111b1, 111a2, and a second friction interface being provided between the first and third brake discs 111b1, 111a3 so that rotation of the first brake disc 111b1 in relation to the second and third brake discs 111a2, 111a3 activates the first and second friction interfaces to provide part of the brake torque.

The first brake disc 111b1 being rotatable in relation to the second brake disc 111a2 and the third brake disc 111a3 is realized by the first brake disc 111b1 being attached to the first control wheel 101 by the control wheel grooves 113a and the second and third brake discs 111a2, 111a3 being attached to the disc holder 108a by the disc holder grooves 109a as described above. The disc holder 108a is attached to the center shaft 103 via the center shaft grooves 114, the center shaft 103 being fixed in the handle 2 and being rotatably fixed relative to the handle 2.

In the embodiment shown, the control system 100 comprises a total of six brake discs distributed with three discs in each of the sets 111a, 111b, where the entire stack of brake discs 111 is provided in a similar manner, i.e. so that such friction interfaces are provided between adjacent brake discs, and the first set of brake discs 111a being provided similarly to the second and third brake discs 111a2 and 111a3, and the brake discs of the second set 111b being provided similarly to 111b1. That is, the brake discs are arranged in the stack 111 so that every other brake disc i.e. brake discs 111b, are fixed to and rotate with the first control wheel 101, and the remaining brake discs, i.e. brake discs 111a, are fixed to the disc holder 108a which is non-rotatably fixed to the center shaft 103. As the center shaft 103 is non-rotatably fixed to the handle 2, the first control wheel 101 and connected brake discs 111b may be rotated relative to the center shaft 103 (and handle) to rotate the first wire drum 102a and control the bending operation of the endoscope 1. To guide and facilitate rotation of the first wire drum 102a and first control wheel 101, the first wire drum 102a and first control wheel 101 are journaled in an inner bearing member 120a. In other embodiments, alternative suitable bearing devices may be applied. The stack 111 may alternatively consist of three, four, five, seven, eight, nine, ten, or more brake discs.

The first of the brake discs 111b1 is positioned between the second and third brake discs 111a2, 111a3 so that the first and second friction interfaces are activated in the braking state of the multi-disc brake 110a and are at least partly released or deactivated in the released state of the multi-disc brake 110a. The friction interfaces include parts of two opposed major surfaces of the first brake disc 111b1, these major surfaces facing corresponding major surfaces of the second and third brake discs 111a2, 111a3, respectively, the friction interfaces similarly including parts of the associated second and third brake disc major surfaces.

Remaining brake discs 111b4, 111b6, and 111a5 of the stack 111 are arranged in a corresponding manner. Thus, the brake disc 111b4 is positioned between the brake discs 111a3, 111a5 so that corresponding friction interfaces are correspondingly and simultaneously activated in the braking state of the multi-disc brake 110a and are at least partly released or deactivated in the released state of the multi-disc brake 110a. These friction interfaces correspondingly include parts of two opposed major surfaces of the brake disc 111b4, these major surfaces facing corresponding major surfaces of the brake discs 111a3, 111b2, the friction interfaces similarly including parts of the associated brake disc major surfaces.

When moving the multi-disc brake 110a from the released state to the braking state by rotation of the knob 104a, a force is exerted on the stack of discs 111 by the sliding member 106a, the force pushing the second and third discs 111a2, 111a3 towards the first disc 111b1, the first and second friction interfaces thereby providing the brake force against rotation of the first brake disc 111b1 relative to the second and third brake discs 111a2, 111a3. Similar action occurs throughout the rest of the stack 111.

The center shaft comprises a frame 115 fixed to the endoscope handle 2 by means of screws (not shown) and via the inner bearing element 120a, the rotation of the first control wheel 101 occurring relative to the frame 115. The first brake disc 111b1 is rotationally fixed relative to the first control wheel 101, and the second and third brake discs 111a2, 111a3 are rotationally fixed relative to the frame 115.

As best seen in FIG. 3, the handle housing 116 forms a handle shell encasing parts of the control system 100. Both the frame 115 and the housing 116 are manufactured of a rigid plastic polymer in the form of ABS.

The brake discs of each set 111a, 111b are manufactured from different materials, i.e. contiguous brake discs are of different materials. Hereby, friction properties of the friction interfaces between adjacent brake discs is controlled. In particular, by selecting suitable different materials, static friction is lowered, improving control of the bending operation. PC is selected for the first set 111a, and ABS for the other set of brake discs 111b. The brake discs of the sets 111a, 111b may alternatively be made from other plastic polymer materials as disclosed above. In other embodiments, one or more of the brake discs of the sets 111a, 111b alternatively or additionally comprise or consist of a metal or metal alloy, such as steel, which may provide higher thermal conductivity. In some embodiments, one of the abovementioned brake discs of the sets 111a, 111b may be of the plastic polymer material, and the other set of the metal.

As seen in FIGS. 3 and 12, the control system 100 further comprises a helical compression spring 117a positioned between the base of the first control wheel 101 and a spring holder 119a coaxially with the center shaft 103 of the control system 100 and the first control wheel 101. The spring 117a exerts a spring force on the stack 111 of brake discs 111a, 111b in the braking state of the multi-disc brake 110a. The helical spring 117 is prestressed and is of steel. In other embodiments, any other suitable spring, e.g. a diaphragm spring, cup spring, disc spring, saucer spring, or leaf spring may be applied instead. The spring can alternatively be provided by one or more of the brake discs, e.g. the first brake disc 111b1, or one of the brake disc sets 111a, 111b, being of a resilient material, such as a resin or spring steel, and other discs or the other set of brake discs being of a substantially non-resilient material, such as non-spring steel. In other embodiments still, alternatively to a compression spring, the spring can be a tension spring or a drive spring in which case the action of the 105a and 106a may be reversed. The control system 100 can also include two or more springs for each brake 110a, 110b, which may be helical and/or compression springs, or a combination of the above spring types may be used. In other embodiments, instead of a spring, other means for activating the braking function of the stack of brake discs can be provided. Such other means may include an element, which can move a brake disc positioned at an end of the stack towards the other brake discs of the stack to provide the brake torque without providing a spring function. Such an element could be activated by a brake handle moving this element between braking and released states.

Figure 14:
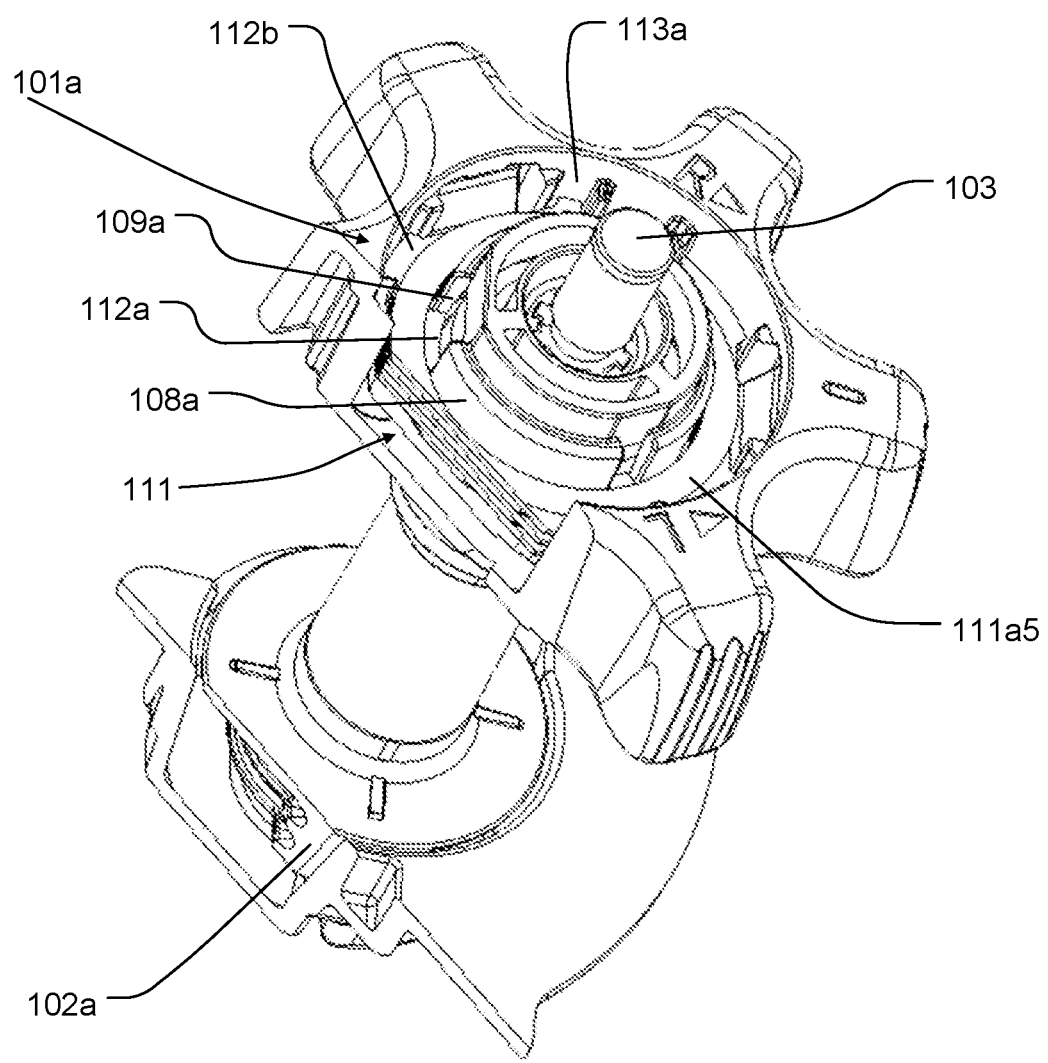
FIG. 14 shows a perspective view of a detail of the control system of FIG. 2 with some parts removed and parts of the brake of FIG. 12 shown in an assembled state.
Figure 15:
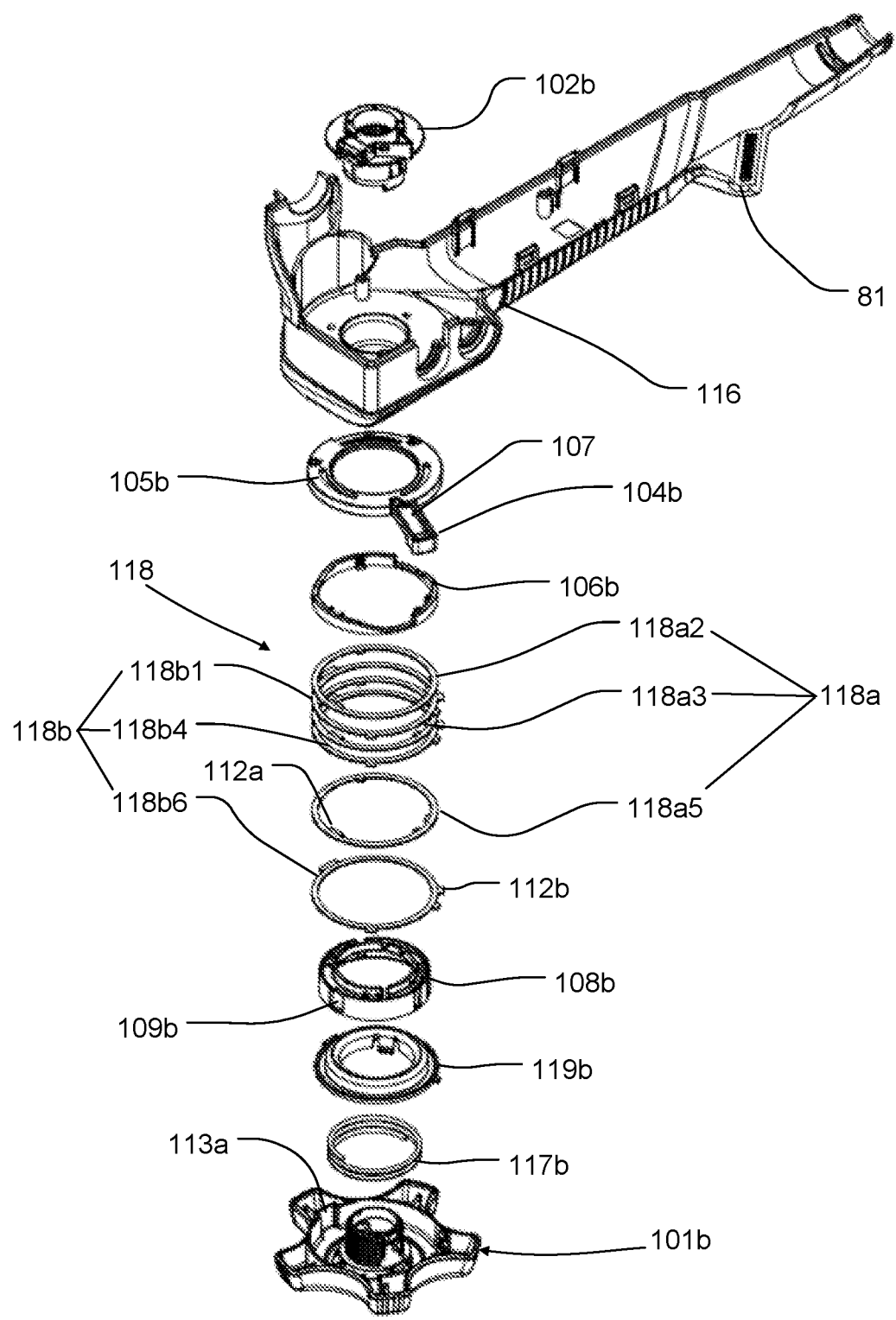
FIG. 15 shows an exploded perspective view of parts of the endoscope of FIG. 1, including of a second multi-disc brake of the second control wheel.

Referring especially to FIG. 14, the control system 100 comprises a further, second control wheel 102 connected to a further or second wire drum 102b for connection to a further steering wire of the endoscope 1, whereby rotation of the second control wheel 102 controls the bending operation in another dimension than that of the first control wheel 101. The control system 100 also comprises a further, second multi-disc brake 110b comprising a stack 118, similarly with two brake disc sets 118a, 118b arranged similarly to the brake discs 111a, 111b of stack 111, wherein activation of the further multi-disc brake 110b similarly changes the multi-disc brake 110b from a released state to a braking state, a brake torque generated by the multi-disc brake 110b in the braking state preventing rotation of the second control wheel 102, the brake torque in the released state being at least partially released. The second control wheel 102, second wire drum 102b, associated steering wire (not shown), and multi-disc brake 110b are embodied as in the first control wheel 101, first wire drum 102a, associated steering wire, and multi-disc brake 110a, respectively. Similar components and features of the further second control wheel 102 have been given similar reference numbers as for the first control wheel 101 described above. For the second control wheel 102, instead of a control knob 104a, the activation of the multi-disc brake 110b is achieved by moving a brake handle 104b into an activation position. The brake handle 104b is positioned attached to a second rotation member 105b and positioned so that the brake handle 104b does not touch the second control wheel 102 during the movement of the brake handle 104b. The brake handle 104b comprises an arm 107 that extends to the multi-disc brake 110b. Additionally, positioned adjacent the second rotation member 105b and adjacent the disc stacks 118a, 118b, is a second sliding member 106b. Similar to brake discs 111a, 111b, every other brake disc i.e. brake discs 118b, are fixed to and rotate with the second control wheel 102, and the remaining brake discs, i.e. brake discs 118a, are fixed to a second disc holder 108b where disc protrusions 112b engage disc holder grooves 109b. The second disc holder 108b is non-rotatably fixed to the center shaft 103. As the center shaft 103 is non-rotatably fixed to the handle 2, the second control wheel 102 and connected brake discs 118b may be rotated relative to the center shaft 103 (and handle) to rotate the second wire drum 102b and control the bending operation of the endoscope 1.

To guide and facilitate rotation of the second wire drum 102b and second control wheel 102, the second wire drum 102b and second control wheel 102 are journaled in an outer bearing element 120b similar to the inner bearing element 120a described above. The outer bearing element 120b is provided in one piece with the handle housing 116. In other embodiments, alternative suitable bearing devices may be applied.

The second control wheel 102 is positioned coaxially with and axially shifted in relation to the first control wheel 101. A diameter of the second control wheel 102 is larger than a diameter of the first control wheel 101 so that the outer one of the two control wheels 101*a*, 101*b* has a smaller diameter.

In the shown embodiment, the endoscope 1 is a gastroscope. In other embodiments, the endoscope 1 may be a duodenoscope or a colonoscope or any other type of endoscope.

In other embodiments, the control wheels, wire drums, and multi-disc brakes are embodied differently from each other.

In other embodiments, only a single control wheel and a single associated multi-disc brake is included in the control system.

The foregoing aspects are further embodied in the following exemplary items:

Item 1. An endoscope control system for performing a bending operation in a disposable insertion endoscope, the endoscope control system comprising: a control wheel connected to a wire drum for connection to a steering wire of the endoscope, whereby rotation of the control wheel controls the bending operation.

Item 2. The control system of item 1, further comprising a multi-disc brake comprising a stack of at least three brake discs, wherein activation of the multi-disc brake changes the multi-disc brake from a released state to a braking state, a brake torque generated by the multi-disc brake in the braking state braking rotation of the control wheel, the brake torque in the released state being at least partially released.

Item 3. The control system of item 2, wherein the stack includes a first brake disc positioned between a second and a third brake disc of the stack, the first brake disc being rotatable in relation to the second and third brake discs, a first friction interface being provided between the first and second discs and a second friction interface being provided between the first and third brake discs, so that rotation of the first brake disc in relation to the second and third brake discs activates the first and second friction interfaces to provide at least part of the brake torque.

Item 4. The control system of item 3, wherein, when moving the multi disc brake from the released state to the braking state, a force is exerted on the stack of discs, the force pushing the second and third discs towards the first disc, the first and second friction interfaces thereby providing a brake force against rotation of the first brake disc relative to the second and third brake discs.

Item 4. The control system of item 2 or 3, further comprising a frame, the rotation of the control wheel occurring relative to the frame, and wherein the first brake disc is rotationally fixed relative to the control wheel, and the second and third brake discs are rotationally fixed relative to the frame.

Item 5. The control system of item 4, wherein the frame is fixed to or forms part of an endoscope handle housing of an endoscope handle.

Item 6. The control system of any one of the previous items, wherein the stack consists of six brake discs.

Item 7. The control system of any one of the previous items, wherein every other of the brake discs of the stack is manufactured from a material different from a material of the remaining brake discs.

Item 8. The control system of any one of the previous items, wherein at least one of the brake discs is manufactured from plastic polymer material.

Item 9. The control system of any one of the previous items, further comprising a spring exerting a spring force on the stack of brake discs in the engaged state of the multi-disc brake.

Item 10. The control system of item 9, wherein the spring is prestressed.

Item 11. The control system of any one of the previous items, further comprising a further control wheel connected to a further wire drum for connection to a further steering wire of the endoscope, whereby rotation of the further control wheel controls the bending operation in another dimension than that of the control wheel; and a further multi-disc brake comprising a stack of at least three brake discs, wherein activation of the further multi-disc brake changes the further multi-disc brake from a released state to a braking state, a brake torque generated by the further multi-disc brake in the braking state braking rotation of the further control wheel, the brake torque in the released state being at least partially released.

Item 12. The control system of any one of the previous items, further comprising a brake handle, movement of which changes the multi-disc brake between the braking state and the released state.

Item 13. The control system of item 12, wherein the movement of the brake handle is transferred to the multi-disc brake by the brake handle rotating a rotation member, such as a disc, relative to a sliding member, such as a disc or one of the brake discs, the sliding member providing a pushing force on at least one of the brake discs activating the braking torque on the multi-disc brake.

Item 14. The control system of item 13, wherein the rotation member and/or the sliding member may include an inclined portion or ramp so that rotating movement between the member along the inclined portion pushes the two members away from each other.

Item 15. An endoscope handle for an endoscope, the endoscope handle comprising a control system according to any one of the previous claims.

Item 16. An endoscope comprising a control system of any one of claims 1 to 14 and/or comprising an endoscope handle of item 15.

Item 17. The endoscope of item 16, further comprising a distal tip or tip part that comprises a bending section connected to the steering wire(s) so that the control system can activate a bending operation of the bending section via the steering wire(s).

Item 18. A method of assembly of an endoscope control system as in any of the preceding items, the endoscope control system being for performing a bending operation in a disposable insertion endoscope, wherein the endoscope control system comprises: a housing frame for forming or for forming part of an endoscope handle housing, the housing frame comprising a connection hole; a first control wheel unit comprising a first wheel handle; a second control wheel unit comprising a second wheel handle; a first shaft unit, the first shaft unit comprising a first wire drum and a first shaft, the first shaft connecting the first control wheel unit to the first wire drum, the first wire drum being for connection to a first steering wire of the endoscope, whereby rotation of the first wheel handle relative to the housing frame about an axis of rotation controls the bending operation in a first dimension; a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension; and wherein the method of assembly comprises, in sequence: 1) holding the first control wheel unit in a position; 2) moving the second control wheel unit in an assembly direction to position the second control wheel unit on the first control wheel unit; 3) moving the housing frame in the assembly direction to position the housing frame on the second control wheel unit; 4) moving the second shaft unit in the assembly direction so that the second shaft is positioned to extend through the connection hole of the housing frame and snaps into engagement with the second control wheel unit by means of a second snap connection between the second shaft and the second control wheel unit; and 5) moving the first shaft unit in the assembly direction so that the first shaft is positioned to extend through the connection hole of the housing frame and through the second shaft and snaps into engagement with the first control wheel unit by means of a first snap connection between the first shaft and the first control wheel unit; whereby the first and second control wheel units, the housing frame, and the first and second shaft units are maintained in position relative to each other in the assembly direction by means of the first and second snap connections.

Item 19. The method of item 18, wherein all the movements of steps 2) to 5) are carried out from one side only.

Item 20. The method of item 18 or 19, wherein, in each of steps 2) to 5), all already positioned parts of the control system to be assembled remain in a held position.

Item 21. The method of any one of the previous items, wherein only the movement carried out in steps 4) and 5) affect the attachment of the parts assembled in steps 1) to 5) to each other.

Item 22. The method of any one of the previous items, wherein, during the sequence of steps 1) to 5), no separate locking device is applied to attach the parts to each other.

Item 23. The method of any one of the previous items, wherein the first and second snap connections are provided only by snap connection parts provided in one piece with the first shaft unit, the first control wheel unit, the second shaft unit, and the second control wheel unit, respectively.

Item 24. The method of any one of the previous items, wherein the first snap connection comprises at least one primary connector part forming part of the first shaft unit and at least one secondary connector part forming part of the first control wheel unit, the primary and secondary connector parts in step 5) snapping directly onto each other to form the first snap connection; and wherein the second snap connection comprises at least one tertiary connector part forming part of the second shaft unit and at least one quaternary connector part forming part of the second control wheel unit, the tertiary and quaternary connector parts in step 4) snapping directly onto each other to form the second snap connection.

Item 25. The method of any one of the previous items, wherein no further steps are involved in the method during the sequence of steps 1) to 5).

Item 26. The method of any one of the previous items wherein, before step 1), the first wheel is positioned in a jig, the first wheel being held in the jig in step 1) and during the sequence of steps 2) to 5).

Item 27. An endoscope control system for performing a bending operation in a disposable insertion endoscope, wherein the endoscope control system comprises: a housing frame for forming or for forming part of an endoscope handle housing, the housing frame comprising a connection hole; a first control wheel unit comprising a first wheel handle; a second control wheel unit comprising a second wheel handle; a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension; wherein the second control wheel is positioned between the first control wheel and the housing frame, the second shaft extends through the connection hole of the housing frame, and the first shaft extends through the connection hole of the housing frame and through the second shaft; and wherein the first shaft is connected to the first control wheel unit by means of a first snap connection between the first shaft and the first control wheel unit, and the second shaft is connected to the second control wheel unit by a second snap connection between the second shaft and the second control wheel unit, whereby the first and second snap connections attach the first and second control wheels, the housing frame, and the first and second shaft units to each other.

Item 28. The control system according to item 27, wherein the first and second snap connections maintain attachment between the first and second control wheels, the housing frame, and the first and second shaft units if all other parts are removed.

Item 29. The control system according to item 27 or 28, wherein the first and second snap connections are provided by snap connection parts provided in one piece with the first shaft unit, the first control wheel unit, the second shaft unit, and the second control wheel unit, respectively.

Item 30. The endoscope control system according to any one of items 27 to 29, wherein the endoscope control system has been assembled according to the method of any one of items 18 to 26.

Item 31. An endoscope comprising the control system assembled according to any one of items 18 to 26 and/or comprising the control system according to any one of items 27 to 30.

Item 32. The endoscope according to item 27, further comprising the first and second steering wires and a distal tip or tip part that comprises a bending section connected to the first and second steering wires so that the control system can activate the bending operation of the bending section via the steering wires.

Item 33. The endoscope according to item 27, wherein the first shaft includes a bearing surface, the second shaft includes an outer bearing surface positioned farther from the axis of rotation than the bearing surface of the first shaft, and the handle housing includes an outer bearing element comprising an inner bearing surface positioned farther from the axis of rotation than the outer bearing surface of the second shaft, the inner bearing surface of the outer bearing element abutting the outer bearing surface of the second shaft so that rotation of the second control wheel is at least partly borne on the outer bearing element.

Item 34. The endoscope of item 33, further comprising an inner bearing element framed disposed at least in part between the first shaft and the second shaft, wherein the inner bearing element frame axially separates the first and second control wheel units from each other.

LIST OF REFERENCE NUMERALS

1 Endoscope
2 Endoscope handle

3 Elongated insertion tube
3a Proximal end of insertion tube
3b Distal end of insertion tube
4 Tip
5 Bending section
6 Suction connector
81 Sampling connector
100 Endoscope control system
101a First control wheel
101b Second control wheel
102a First wire drum
102b Second wire drum
103 Center shaft
104a Brake knob
104b Brake handle
105a Rotation member
106a Sliding member
106b Sliding member
107 Arm
108a Disc hold
108b Disc hold
109a Disc holder grooves
109b Disc holder grooves
110a First multi-disc brake
110b Second multi-disc brake
111 Stack of brake discs
111a Set of inner brake discs
111a2 Inner brake disc
111a3 Inner brake disc
111a4 Inner brake disc
111b Set of outer brake discs
111b1 Outer brake disc
111b4 Outer brake disc
111b6 Outer brake disc
112a Inner brake disc protrusion
112b Outer brake disc protrusion
113a Control wheel grooves
114 Center shaft grooves
115 Frame
116 Handle housing
117a Spring
117b Spring
118 Stack of brake discs
118a Set of inner brake discs
118b Set of outer brake discs
119a Spring holder
119b Spring holder
120a Inner bearing element
120b Outer bearing element
120c Inner bearing surface of inner bearing element
120d Inner bearing surface of outer bearing element
120e Sleeve part
121 Inner bearing element frame
122 Screw hole
D Assembly direction

The invention claimed is:

1. An endoscope control system for performing a bending operation in a disposable insertion endoscope, the endoscope control system comprising:
a first control wheel connected to a first wire drum for connection to a steering wire of the endoscope, whereby rotation of the first control wheel controls the bending operation, the first control wheel including a radially inwardly extending longitudinal groove; and
a rotation member and a sliding member, the rotation member and/or the sliding member including an inclined portion or ramp so that rotation of the rotation member pushes the sliding member toward the first control wheel;
a disc holder including a radially outwardly facing longitudinal groove; and
a multi-disc brake comprising a stack of at least three brake discs, the stack including a first brake disc, a second brake disc and a third brake disc, the first brake disc positioned between the second brake disc and the third brake disc, and the stack positioned between the sliding member and the first control wheel,
the second brake disc and the third brake disc each including a radially inwardly extending protrusion configured to engage the radially outwardly facing longitudinal groove of the disc holder,
the first brake disc including a radially outwardly facing protrusion configured to engage the radially inwardly extending longitudinal groove of the first control wheel,
wherein rotation of the rotation member pushes the sliding member toward the first control wheel and causes the sliding member to exert a compressive force onto the stack and change the multi-disc brake from a released state to a braking state, a brake torque generated by the multi-disc brake in the braking state preventing rotation of the first control wheel, the brake torque in the released state being at least partially released.

2. The control system according to claim 1, wherein a first friction interface is provided between the first and second discs and a second friction interface is provided between the first and third brake discs, so that rotation of the first brake disc in relation to the second and third brake discs activates the first and second friction interfaces to provide at least part of the brake torque.

3. The control system according to claim 2, wherein, when moving the multi-disc brake from the released state to the braking state, a force is exerted on the stack of discs, the first and second friction interfaces providing a brake force against rotation of the first brake disc relative to the second and third brake discs.

4. The control system according to claim 2, further comprising a frame, the rotation of the first control wheel occurring relative to the frame, and wherein the first brake disc is rotationally fixed relative to the first control wheel, and the second and third brake discs are rotationally fixed relative to the frame.

5. The control system according to claim 4, wherein the frame is fixed to or forms part of an endoscope handle housing of an endoscope handle.

6. The control system according to claim 1, wherein the stack consists of six brake discs.

7. The control system according to claim 6, wherein every other of the brake discs of the stack is manufactured from a material different from a material of the remaining brake discs.

8. The control system according to claim 1, wherein at least one of the brake discs is manufactured from plastic polymer material.

9. The control system according to claim 1, further comprising a spring exerting a spring force on the stack of brake discs in the braking state of the multi-disc brake.

10. The control system according to claim 9, wherein the spring is prestressed.

11. The control system according to claim 1, further comprising a second control wheel connected to a second wire drum for connection to a further steering wire of the endoscope, whereby rotation of the second control wheel controls the bending operation in another dimension than that of the first control wheel; and a second multi-disc brake comprising a stack of at least three brake discs, wherein activation of the second multi-disc brake changes the second multi-disc brake from a released state to a braking state, a brake torque generated by the second multi-disc brake in the braking state braking rotation of the second control wheel, the brake torque in the released state being at least partially released.

12. The control system according to claim 11, further comprising a brake handle, movement of which changes the second multi-disc brake between the braking state and the released state.

13. The control system according to claim 12, wherein the movement of the brake handle is transferred to the second multi-disc brake by the brake handle rotating a second rotation member relative to a second sliding member, the second sliding member providing a pushing force on at least one of the brake discs activating the braking torque on the second multi-disc brake.

14. The control system according to claim 13, wherein the second rotation member and/or the second sliding member includes an inclined portion or ramp so that rotating movement between the second rotation member and the second sliding member pushes the second rotation member and the second sliding member away from each other.

15. An endoscope handle for an endoscope, the endoscope handle comprising a control system according to claim 1.

16. The endoscope handle of claim 15, further comprising the first control wheel rotatably coupled to the first wire drum, wherein rotation of the first control wheel rotates the first wire drum, a second control wheel rotatably coupled to a second wire drum, wherein rotation of the second control wheel rotates the second wire drum, and wherein the rotation of the first wire drum and the second wire drum controls the bending operation.

17. An endoscope comprising an endoscope handle according to claim 15.

18. The endoscope according to claim 17, further comprising a distal tip or tip part that comprises a bending section connected to the steering wire(s) so that the control system can activate a bending operation of the bending section via the steering wire(s).

19. The endoscope according to claim 17, further comprising:
a housing frame for forming or for forming part of an endoscope handle housing, the housing frame comprising a connection hole;
a first control wheel unit comprising a first wheel handle;
a second control wheel unit comprising a second wheel handle;
a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension;
wherein the second control wheel is positioned between the first control wheel and the housing frame, the second shaft extends through the connection hole of the housing frame, and the first shaft extends through the connection hole of the housing frame and through the second shaft; and
wherein the first shaft is connected to the first control wheel unit by means of a first snap connection between the first shaft and the first control wheel unit, and the second shaft is connected to the second control wheel unit by a second snap connection between the second shaft and the second control wheel unit,
whereby the first and second snap connections attach the first and second control wheels, the housing frame, and the first and second shaft units to each other.

20. The endoscope according to claim 19, wherein the first shaft includes a bearing surface, the second shaft includes an outer bearing surface positioned farther from the axis of rotation than the bearing surface of the first shaft, and the handle housing includes an outer bearing element comprising an inner bearing surface positioned farther from the axis of rotation than the outer bearing surface of the second shaft, the inner bearing surface of the outer bearing element abutting the outer bearing surface of the second shaft so that rotation of the second control wheel is at least partly borne on the outer bearing element.

21. The control system according to claim 1, wherein the stack of at least three brake discs comprises a first brake disc set and a second brake disc set,
wherein the brake discs of the first brake disc set are interlaced with the brake discs of the second brake disc set and each includes a radially inwardly extending protrusion configured to engage the radially outwardly facing longitudinal groove of the disc holder, the first brake disc set including the second brake disc and the third brake disc,
wherein the brake discs of the second brake disc set each include a radially outwardly facing protrusion configured to engage the radially inwardly extending longitudinal groove of the first control wheel, the second brake disc set including the first brake disc.

22. The control system according to claim 21, wherein the stack of at least three brake discs comprises at least six brake discs, and wherein the brake discs of the first brake disc set or the second brake disc set comprise a polymeric material.

* * * * *